US012797467B2

(12) United States Patent
Zhang et al.

(10) Patent No.: US 12,797,467 B2
(45) Date of Patent: Nov. 17, 2026

(54) BISPECIFIC CS1-BCMA CAR-T CELL AND APPLICATION THEREOF

(71) Applicant: WUHAN SIAN BIOTECHNOLOGY CO., LTD., Wuhan (CN)

(72) Inventors: Lianjun Zhang, Wuhan (CN); Heng Mei, Wuhan (CN); Tangyi Zhou, Wuhan (CN); Xiongbo Chen, Wuhan (CN); Wei Xiong, Wuhan (CN)

(73) Assignee: WUHAN SIAN BIOTECHNOLOGY CO., LTD., Wuhan (CN)

( * ) Notice: Subject to any disclaimer, the term of this patent is extended or adjusted under 35 U.S.C. 154(b) by 643 days.

(21) Appl. No.: 18/262,930

(22) PCT Filed: Jan. 26, 2022

(86) PCT No.: PCT/CN2022/074084
§ 371 (c)(1),
(2) Date: Jul. 26, 2023

(87) PCT Pub. No.: WO2022/161409
PCT Pub. Date: Aug. 4, 2022

(65) Prior Publication Data

US 2024/0082401 A1 Mar. 14, 2024

(30) Foreign Application Priority Data

Jan. 29, 2021 (CN) ........................ 202110129564.5

(51) Int. Cl.

| | |
|---|---|
| ***A61K 40/42*** | (2025.01) |
| ***A61K 40/11*** | (2025.01) |
| ***A61K 40/31*** | (2025.01) |
| ***A61P 35/00*** | (2006.01) |
| ***C07K 14/705*** | (2006.01) |
| ***C07K 16/28*** | (2006.01) |

(52) U.S. Cl.
CPC ............ *A61K 40/421* (2025.01); *A61K 40/11* (2025.01); *A61K 40/31* (2025.01); *A61K 40/4215* (2025.01); *A61P 35/00* (2018.01); *C07K 14/7051* (2013.01); *C07K 16/2803* (2013.01); *C07K 16/2878* (2013.01); *A61K 2239/29* (2023.05); *C07K 2317/31* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | | |
|---|---|---|---|---|
| 12,540,195 B2 * | 2/2026 | Wu | .................... | C07K 14/7051 |
| 2019/0135894 A1 | 5/2019 | Ma et al. | | |
| 2019/0216851 A1 | 7/2019 | Xiao et al. | | |
| 2019/0255108 A1 | 8/2019 | Ma et al. | | |
| 2021/0015870 A1 * | 1/2021 | Wu | .................. | C07K 14/70578 |

FOREIGN PATENT DOCUMENTS

| | | | |
|---|---|---|---|
| CN | 105384825 A | 3/2016 | |
| CN | 107849112 A | 3/2018 | |
| CN | 109562126 A | 4/2019 | |
| CN | 111247242 A | 6/2020 | |
| CN | 112074278 A | 12/2020 | |
| CN | 112778427 A | 5/2021 | |
| WO | WO-2019241358 A2 * | 12/2019 | ....... C07K 14/70578 |

OTHER PUBLICATIONS

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084. (Year: 2002).*
Jassaud M, Ziane-Chaouche L, Duhamel M, Salzet M. Innate immune cells in chimeric antigen receptor therapy. Mol Ther. Jan. 7, 2026;34(1):97-116. doi: 10.1016/j.ymthe.2025.10.003. (Year: 2026).*
MacCallum et al. "Antibody-antigen interactions: contact analysis and binding site topography", Journal of Molecular Biology, 1996. vol. 262, pp. 732-745. (Year: 1996).*
Schettini F. et al. Identification of cell surface targets for CAR-T cell therapies and antibody-drug conjugates in breast cancer. ESMO Open. Jun. 2021;6(3):100102. doi: 10.1016/j.esmoop.2021.100102. (Year: 2021).*
Sun D et al. Carâ¢ÂÂt cell therapy: A breakthrough in traditional cancer treatment strategies (Review). Mol Med Rep. Mar. 2024; 29(3):47. doi: 10.3892/mmr.2024.13171 (Year: 2024).*

(Continued)

*Primary Examiner* — Misook Yu
(74) *Attorney, Agent, or Firm* — HSML P.C.

(57) ABSTRACT

The present invention provides a bispecific CS1-BCMA CAR-T cell and an application thereof. Specifically, the present invention provides a bispecific CAR, which comprises CS1 scFv and BCMA scFv, and a 4-1BB co-stimulatory domain and a CD3 activation domain. The bispecific CAR-T cell in the present invention has a significant killing effect on CS1 positive target cells and BCMA positive target cells, and can secrete IFN-γ against target cells and significantly inhibit the growth of RPMI8226 xenograft tumor in an in vivo experiment. The present invention further provides a preparation method and an application of the bispecific CAR-T cell.

17 Claims, 16 Drawing Sheets

Specification includes a Sequence Listing.

(56) References Cited

OTHER PUBLICATIONS

O'Neal, J., Ritchey, J.K., Cooper, M.L et al. CS1 Car-T targeting the distal domain of CS1 (SLAMF7) shows efficacy in high tumor burden myeloma model despite fratricide of CD8+CS1 expressing CAR-T cells. Leukemia 36, 1625-1634 (2022). https://doi.org/10.1038/s41375-022-01559-4 (Year: 2022).*
Dogan A, Siegel D, Tran N, Fu A, Fowler J, Belani R, Landgren O. B-cell maturation antigen expression across hematologic cancers: a systematic literature review. Blood Cancer J. Jun. 30, 2020;10(6):73. doi: 10.1038/s41408-020-0337-y. (Year: 2020).*
Amiri M, Moaveni AK, Majidi Zolbin M, Shademan B, Nourazarian A. Optimizing cancer treatment: the synergistic potential of CAR-T cell therapy and CRISPR/Cas9. Front Immunol. Nov. 8, 2024; 15:1462697. doi: 10.3389/fimmu.2024.1462697. (Year: 2024).*
PDQ Screening and Prevention Editorial Board. Cancer Prevention Overview (PDQÂ®): Health Professional Version. Feb. 12, 2025. In: PDQ Cancer Information Summaries [Internet]. Bethesda (MD): National Cancer Institute (US); 2002-. Available from: https://www.ncbi.nlm.nih.gov/books/NBK66016/ (Year: 2025).*
International Search Report (with English translation) and Written Opinion issued in PCT/CN2022/074084, dated Apr. 24, 2022, 18 pages provided.

* cited by examiner

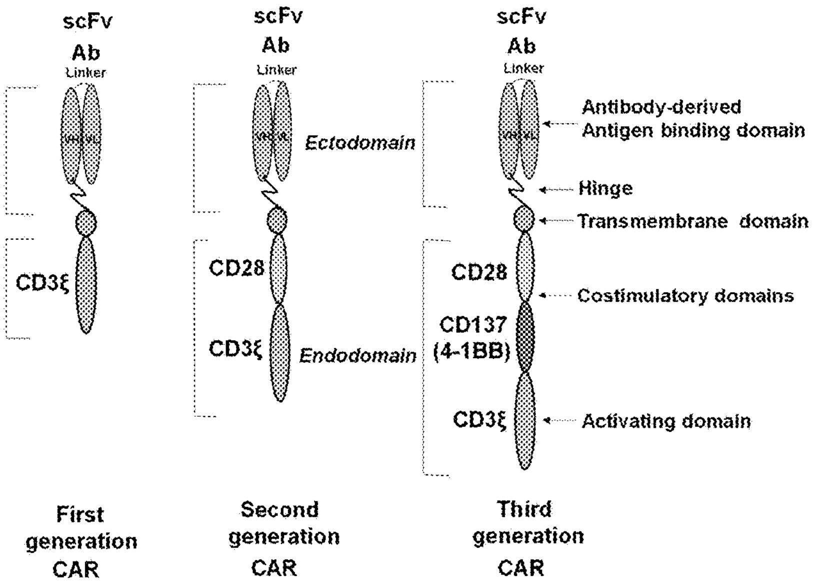

Fig. 1

BCMA Antigen

```
      10         20         30         40         50
MLQMAGQCSQ NEYFDSLLHA CIPCQLRCSS NTPPLTCQRY CNASVTNSVK
       60         70         80         90        100
GTNAILWTCL GLSLIISLAV FVLMFLLRKI NSEPLKDEFK NTGSGLLGMA
      110        120        130        140        150
NIDLEKSRTG DEIILPRGLE YTVEECTCED CIKSKPKVDS DHCFPLPAME
      160        170        180
EGATILVTTK TNDYCKSLPA ALSATEIEKS ISAR  (SEQ ID NO: 13)
```

CS1 Antigen

```
      10         20         30         40         50
MAGSPTCLTL IYILWQLTGS AASGPVKELV GSVGGAVTFP LKSKVKQVDS
       60         70         80         90        100
IVWTFNTTPL VTIQPEGGTI IVTQNRNRER VDFPDGGYSL KLSKLKKNDS
      110        120        130        140        150
GIYYVGIYSS SLQQPSTQEY VLHVYEHLSK PKVTMGLQSN KNGTCVTNLT
      160        170        180        190        200
CCMEHGEEDV IYTWKALGQA ANESHNGSIL PISWRWGESD MTFICVARNP
      210        220        230        240        250
VSRNFSSPIL ARKLCEGAAD DPDSSMVLLC LLLVPLLLSL FVLGLFLWFL
      260        270        280        290        300
KRERQEEYIE EKKRVDICRE TPNICPHSGE NTEYDTIPHT NRTILKEDPA
      310        320        330
NTVYSTVEIP KKMENPHSLL TMPDTPRLFA YENVI  (SEQ ID NO: 12)
```

Fig. 2

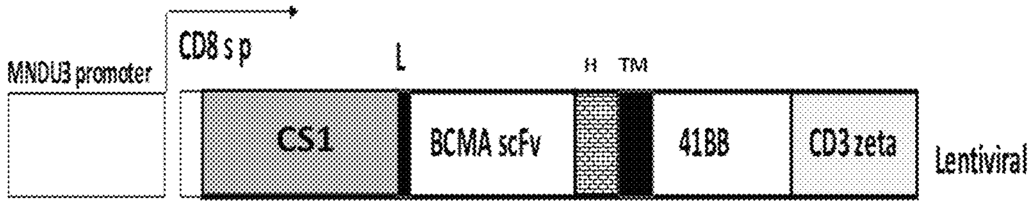

Fig. 3

*VQLQQSGPEVVRPGVSVKISCKGSGYTFTDYAIHWVKQSHAKSLEWIGVINTYNGNTNYNQKFKGKATMTVDK*
*SSSTAYMELARLTSEDSAIYYCTRTGYYYGPSHYFDYWGQGTTLTVSSGGGGSGGGGSGGGGSDIVLTQSPASLT*
*VSLGQRATMSCRASKSVSTSGYSYVHWYQQKPGQPPKLLIYLASNLESGVPARFSASGSGTDFTLNIHPVEEEDA*
*ATYYCQHSRELPWTFGGGTKLEIKR*GGGGSGGGGSGGGGS*DIVMTQSPATLSVTPGDRVSLSCRASQSISDYL*
*HWYQQKSHESPRLLIKYASQSISGIPSRFSGSGSGSDFTLSINSVEPEDVGVYYCQNGHSFPPTFGGGTKLEIKGG*
*GGSGGGGSGGGGSQVQLQQSGPELVKPGASVKMSCKASGYTFTSYVMHWVKQKPGQGLEWIGYIIPYNDAT*
*KYNEKFKGKATLTSDKSSSTAYMELSSLTSEDSAVYYCARYNYDGYFDVWGAGTTVTVSSLE*KTTTPAPRPPTPAP
TIASQPLSLRPEACRPAAGGAVHTRGLDFASDKPFWVLVVVGGVLACYSLLVTVAFIIFWVKRGRKKLLYIFKQPF
MRPVQTTQEEDGCSCRFPEEEEGGCELRVKFSRSADAPAYQQGQNQLYNELNLGRREEYDVLDKRRGRDPEM
GGKPQRRKNPQEGLYNELQKDKMAEAYSEIGMKGERRRGKGHDGLYQGLSTATKDTYDALHMQALPPR

Wherein, the italic part is anti-CS-1 scFv and anti-BCMA scfv, respectively. The "_" part is hinge region, transmembrane domain and costimulatory domain. The "=" part is CD3 ζ activating domain.

Fig. 4

A
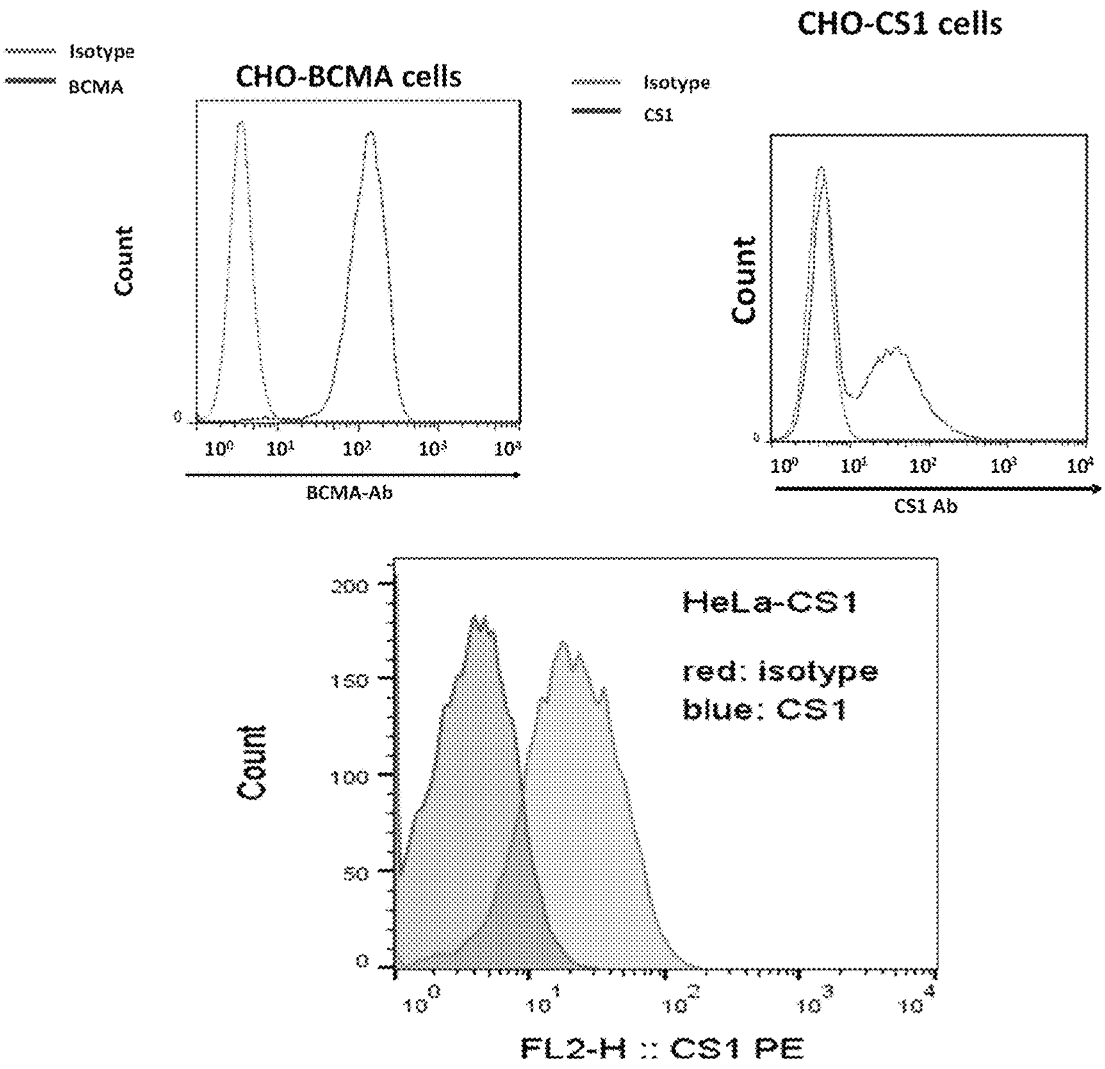
B
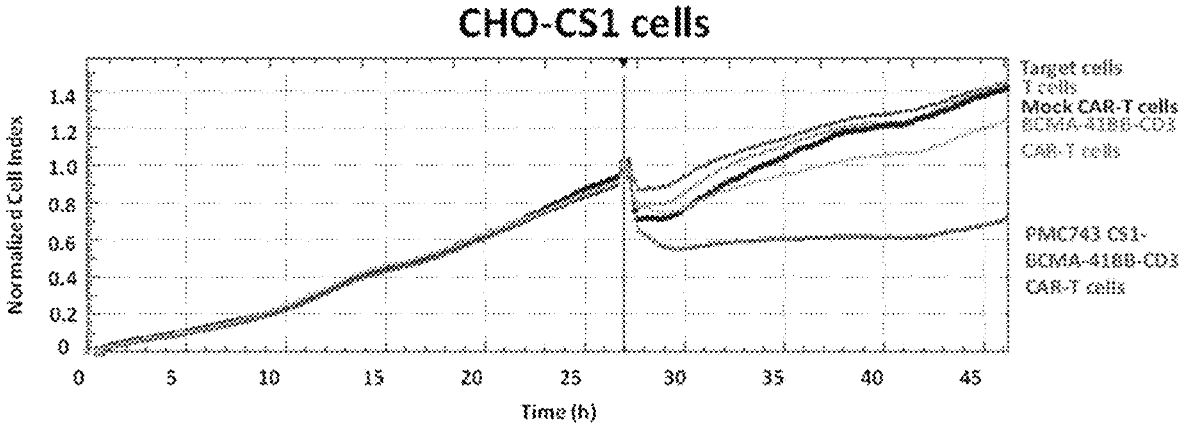
Fig. 6

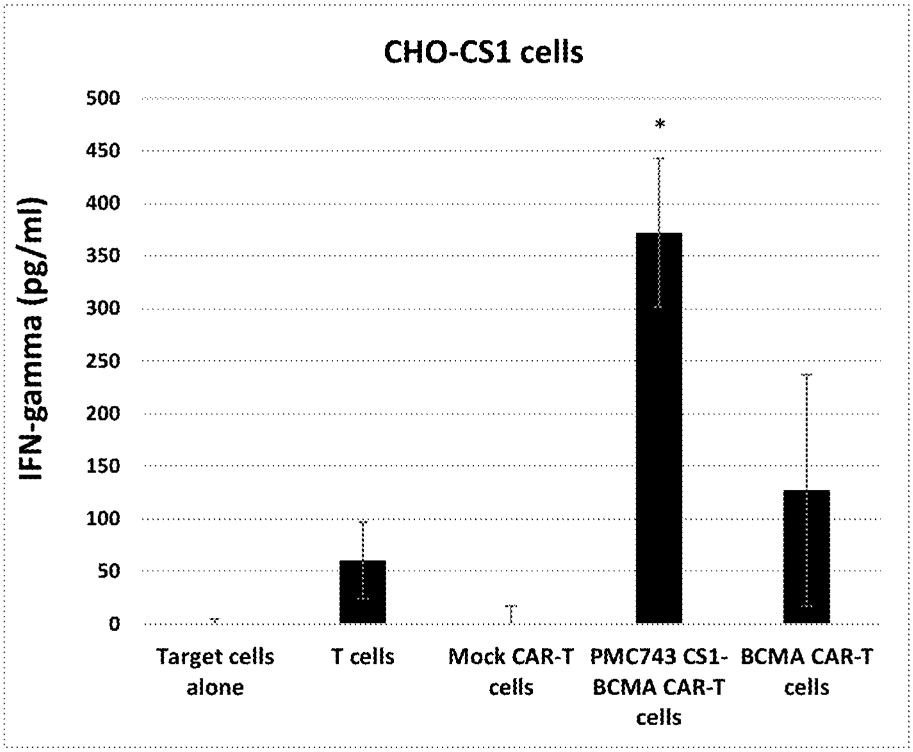
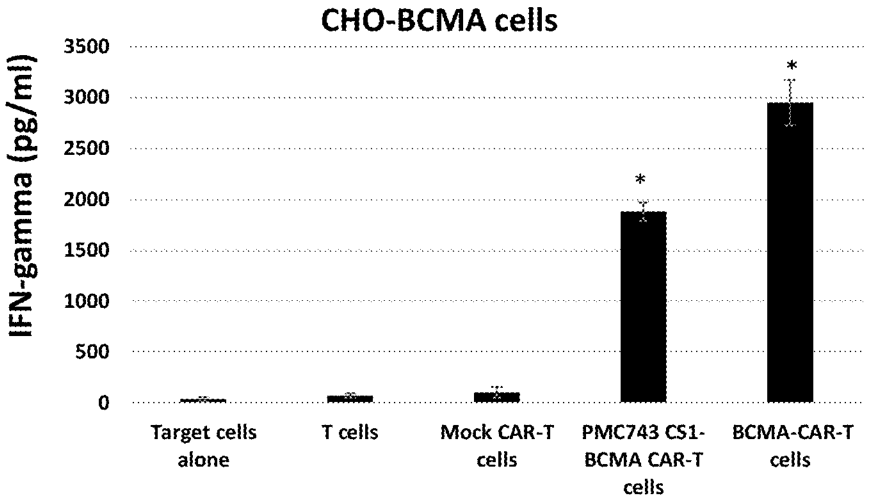
Fig. 10

B. Donor # 890

C. Donor # 999

A. Donor # 57
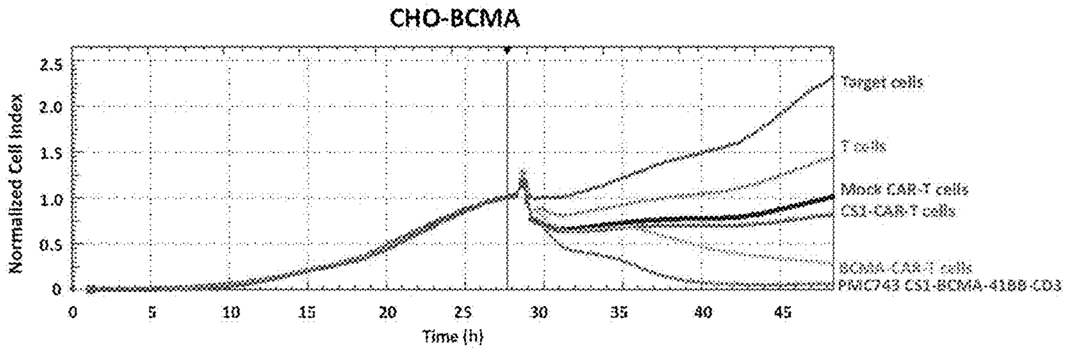
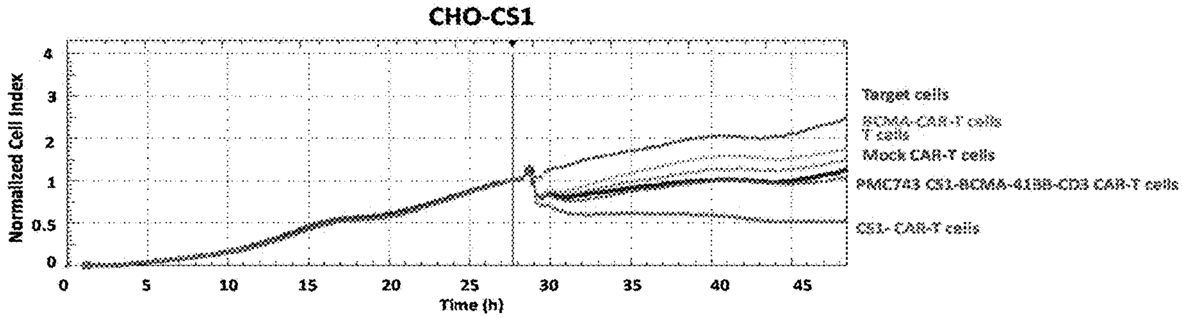
B. Donor # 890
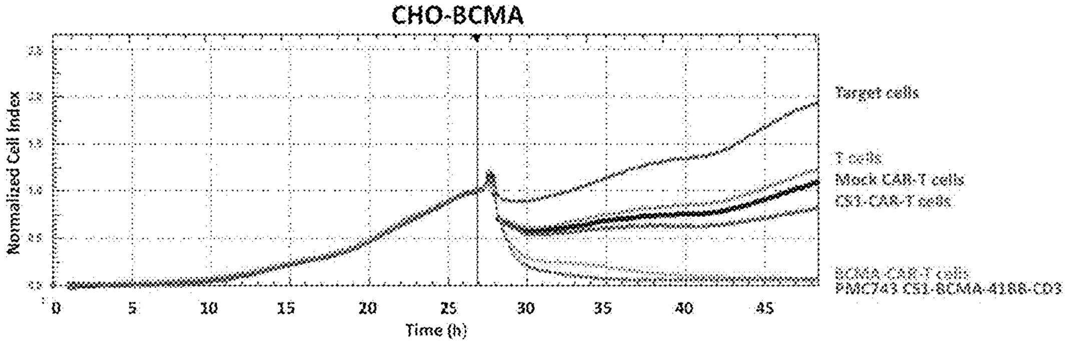
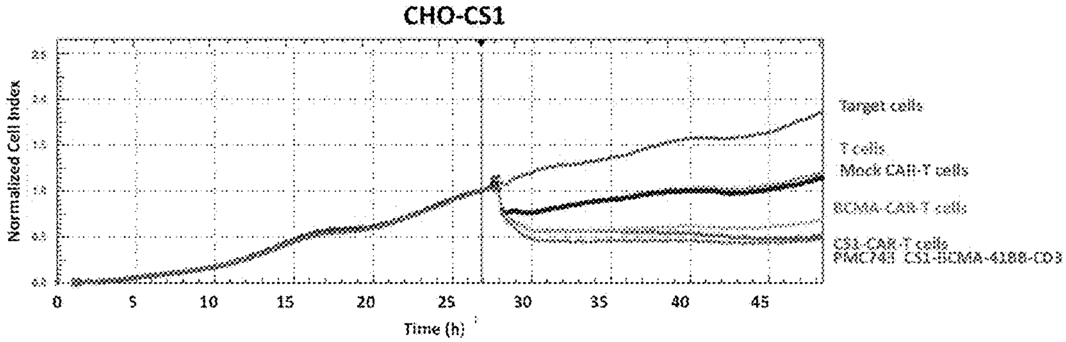
Fig. 13

C. Donor # 999
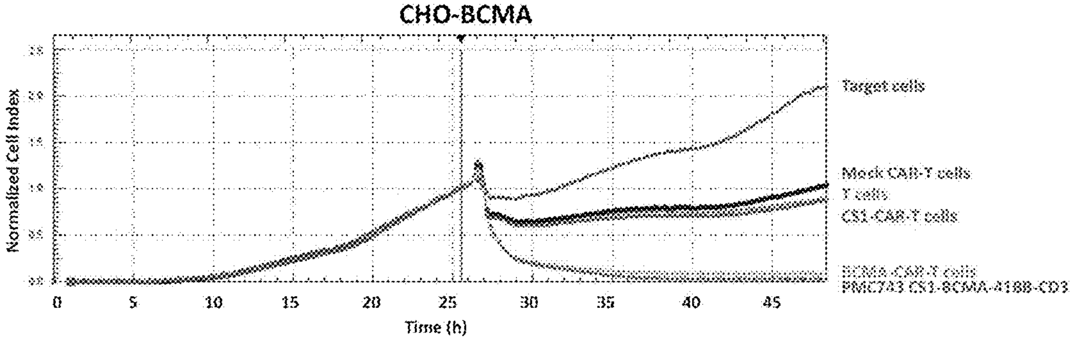
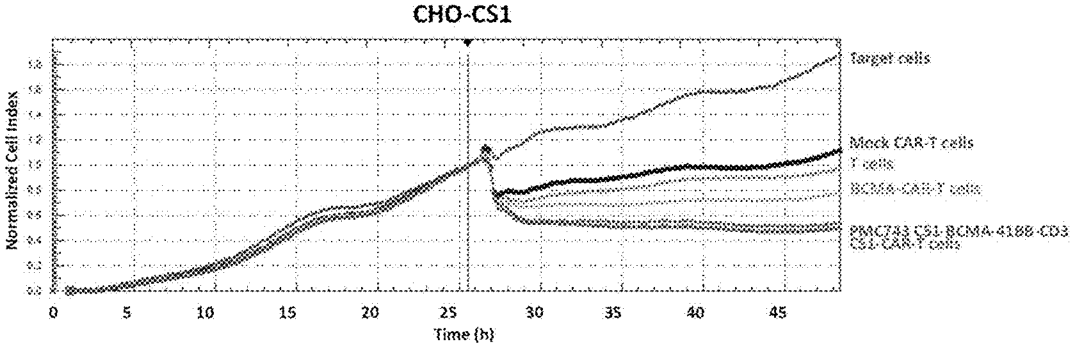
Fig. 13(continued)

A. Donor # 57

B. Donor # 890

C. Donor # 999
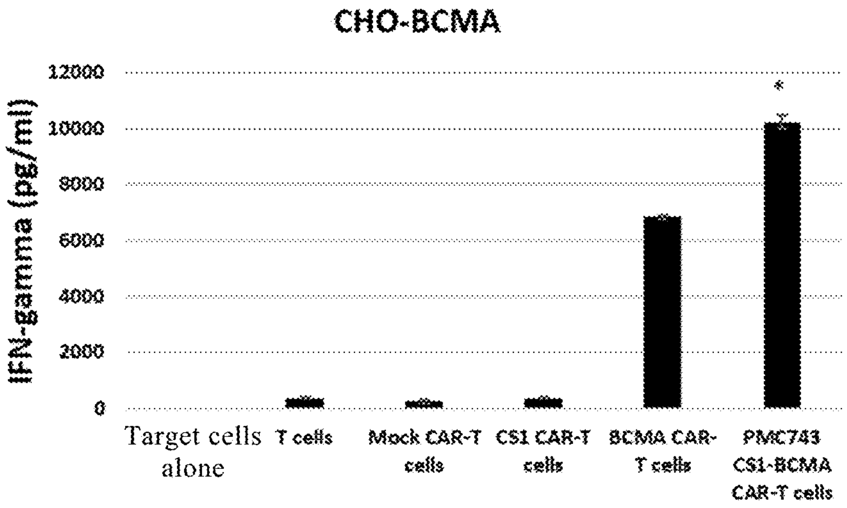
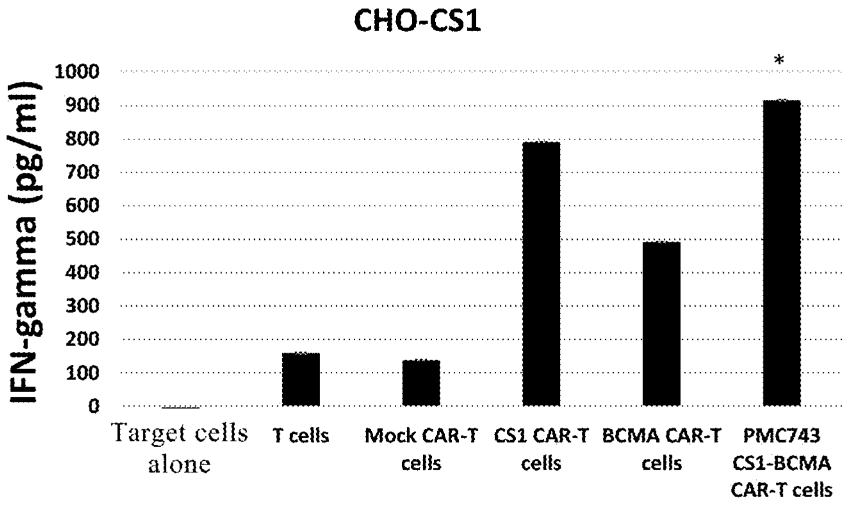
Fig. 14(continued)

BISPECIFIC CS1-BCMA CAR-T CELL AND APPLICATION THEREOF

TECHNICAL FIELD

The present invention relates to the field of biotechnology, in particular to a bispecific CS1-BCMA CAR-T cell and application thereof.

BACKGROUND

Immunotherapy is becoming a very promising cancer therapeutic method. T cells or T lymphocytes are effective weapons for the immune system and can continuously search for foreign antigens or abnormal cells (such as cancer cells or infected cells) from normal cells. Genetic modification of T cells with CAR (chimeric antigen receptor) constructs is the most common method for designing tumor-specific T cells. Transfusing CAR-T cells that target tumor-associated antigen (TAA) into patients (called adoptive cell transfer or ACT) represents an effective immunotherapy method. Compared with chemotherapy or antibodies, the advantage of CAR-T technology is that reprogrammed engineered T cells can proliferate and persist in patients ("living drugs").

Generally, CAR includes a single-chain variable fragment (scFv) derived from a monoclonal antibody at the N-terminus, a hinge region, a transmembrane domain, several intracellular costimulatory domains ((i) CD28, (ii) CD137(4-1BB), CD27 or other costimulatory domains), and a tandem CD3-zeta activating domain (FIG. 1). CAR developed from the first generation (without costimulatory domain) to the second generation (with a costimulatory domain), then to the third generation CAR (with multiple costimulatory domains). CAR with multiple costimulatory domains (i.e., the third generation CAR) can enhance the cytotoxicity of CAR-T cells, significantly improve the persistence of CAR-T cells, and show enhanced anti-tumor activity.

At present, CAR-T therapy still has many challenges for the treatment of solid tumors, including the lack of ideal therapeutic targets, homing disorders, and poor persistence of CAR-T cells caused by immunosuppressive microenvironment. Therefore, there is also a need in the art to develop new CAR-T cells and therapeutic methods for solid tumors.

SUMMARY OF THE INVENTION

The purpose of the present invention is to provide a bispecific CS1-BCMA CAR-T cell and use thereof.

In the first aspect of the present invention, it provides a bispecific chimeric antigen receptor (CAR), and the structure of the chimeric antigen receptor is shown in the following Formula I:

$$\text{L-scFv1-I-scFv2-H-TM-C-CD3}\zeta \qquad \text{(I)}$$

wherein, each "-" is independently a linking peptide or a peptide bond;

L is an optional signal peptide sequence;

I is a flexible linker;

H is an optional hinge region;

TM is a transmembrane domain;

C is a costimulatory signal molecule;

CD3ζ is a cytoplasmic signaling sequence derived from CD3;

one of scFv1 and scFv2 is an antigen binding domain targeting CS1, and the other is an antigen binding domain targeting BCMA.

In another preferred embodiment, the scFv1 is an antigen binding domain targeting CS1, and the scFv2 is an antigen binding domain targeting BCMA.

In another preferred embodiment, the structure of the antigen binding domain targeting CS1 is shown in the following Formula A or B:

$$V_{H1}\text{-}V_{L1} \qquad \text{(A);}$$

$$V_{L1}\text{-}V_{H1} \qquad \text{(B)}$$

wherein, $V_{H1}$ is an anti-CS1 antibody heavy chain variable region; $V_{L1}$ is an anti-CS1 antibody light chain variable region; "-" is a linking peptide or a peptide bond.

In another preferred embodiment, the structure of the antigen binding domain targeting CS1 is as shown in Formula A.

In another preferred embodiment, the $V_{H1}$ and $V_{L1}$ are linked by a flexible linker (or linking peptide), and the flexible linker (or linking peptide) is a sequence of 1-4 consecutive SEQ ID NO: 6(GGGGS), preferably 2-4, more preferably 3-4.

In another preferred embodiment, the amino acid sequence of the anti-CS1 antibody heavy chain variable region is as shown in SEQ ID NO: 1, and the amino acid sequence of the anti-CS1 antibody light chain variable region is as shown in SEQ ID NO: 2.

In another preferred embodiment, the structure of the antigen binding domain targeting BCMA is shown in the following Formula C or D:

$$V_{L2}\text{-}V_{H2} \qquad \text{(C);}$$

$$V_{H2}\text{-}V_{H2} \qquad \text{(D)}$$

wherein, $V_{L2}$ is an anti-BCMA antibody light chain variable region; $V_{H2}$ is an anti-BCMA antibody heavy chain variable region; "-" is the a linking peptide or a peptide bond.

In another preferred embodiment, the structure of the antigen binding domain targeting BCMA is shown in Formula C.

In another preferred embodiment, the $V_{L2}$ and $V_{H2}$ are linked by a flexible linker (or linking peptide), and the flexible linker (or linking peptide) is a sequence of 1-4 consecutive SEQ ID NO: 6 (GGGGS), preferably 2-4, more preferably 3-4.

In another preferred embodiment, the amino acid sequence of the anti-BCMA antibody heavy chain variable region is as shown in SEQ ID NO: 4, and the amino acid sequence of the anti-BCMA antibody light chain variable region is as shown in SEQ ID NO: 5.

In another preferred embodiment, the scFv1 and/or scFv2 are mouse-derived, human-derived, human-derived and mouse-derived chimeric, or fully humanized single-chain antibody variable region fragments.

In another preferred embodiment, the sequence of the flexible linker I comprises a sequence of 2-6, preferably 3-4 consecutive SEQ ID NO: 6 (GGGGS).

In another preferred embodiment, L is a signal peptide of a protein selected from the group consisting of CD8, CD28, GM-CSF, CD4, CD137, and a combination thereof.

In another preferred embodiment, L is a signal peptide derived from CD8.

In another preferred embodiment, the amino acid sequence of L is as shown in SEQ ID NO: 7.

In another preferred embodiment, H is a hinge region of a protein selected from the group consisting of CD8, CD28, CD137, and a combination thereof.

In another preferred embodiment, H is a hinge region derived from CD8.

In another preferred embodiment, the amino acid sequence of H is as shown in SEQ ID NO: 8.

In another preferred embodiment, the TM is a transmembrane region of a protein selected from the group consisting of CD28, CD3 epsilon, CD45, CD4, CD5, CD8, CD9, CD16, GD2, CD33, CD37, CD64, CD80, CD86, CD134, CD137, CD154, and a combination thereof.

In another preferred embodiment, TM is a transmembrane region derived from CD28.

In another preferred embodiment, the amino acid sequence of TM is as shown in SEQ ID NO: 9.

In another preferred embodiment, C is a costimulatory signal molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, and a combination thereof.

In another preferred embodiment, C is a costimulatory signal molecule derived from 4-1BB.

In another preferred embodiment, the amino acid sequence of the 4-1BB-derived costimulatory signal molecule is as shown in SEQ ID NO: 10.

In another preferred embodiment, the amino acid sequence of CD3ζ is as shown in SEQ ID NO: 11.

In another preferred embodiment, the amino acid sequence of the chimeric antigen receptor is as shown in SEQ ID NO: 3.

In the second aspect of the present invention, it provides a nucleic acid molecule encoding the chimeric antigen receptor (CAR) of the first aspect of the present invention.

In another preferred embodiment, the nucleic acid molecule is isolated.

In another preferred embodiment, the 5' end of the nucleic acid molecule further comprises a promoter sequence, preferably an MNDU3 promoter.

In the third aspect of the present invention, it provides a vector comprising the nucleic acid molecule of the second aspect of the present invention.

In another preferred embodiment, the vector is selected from the group consisting of DNA, RNA, a plasmid, a lentiviral vector, an adenovirus vector, an adeno-associated viral vector (AAV), a retroviral vector, a transposon, and a combination thereof.

In another preferred embodiment, the vector is selected from the group consisting of a plasmid and a viral vector.

In another preferred embodiment, the vector is in the form of a viral particle.

In another preferred embodiment, the vector is a lentiviral vector.

In another preferred embodiment, the lentiviral vector comprises a promoter, preferably selected from the group consisting of an MNDU3 promoter, an EF-1 alpha, a CMV promoter, and a combination thereof.

In the fourth aspect of the present invention, it provides a host cell comprising the vector of the third aspect of the present invention, or having the exogenous nucleic acid molecule of the second aspect of the present invention integrated in the chromosome, or expressing the CAR of the first aspect of the present invention.

In another preferred embodiment, the host cell comprises a eukaryotic cell and a prokaryotic cell.

In another preferred embodiment, the host cell comprises *E. coli.*

In the fifth aspect of the present invention, it provides an engineered immune cell that expresses the CAR of the first aspect of the present invention.

In another preferred embodiment, the cell is an isolated cell, and/or the cell is a genetically engineered cell.

In another preferred embodiment, the immune cell is derived from a human or non-human mammal, such as a mouse.

In another preferred embodiment, the cell comprises a T cell, an NK cell.

In another preferred embodiment, the cell is a CAR-T cell or a CAR-NK cell, preferably a CAR-T cell.

In another preferred example, the CAR is co-expressed with a cell suicide element in the immune cell.

In the sixth aspect of the present invention, it provides a formulation comprising the chimeric antigen receptor of the first aspect of the present invention, the nucleic acid molecule of the second aspect of the present invention, the vector of the third aspect of the present invention, or the immune cell of the fifth aspect of the present invention, and a pharmaceutically acceptable carrier, diluent or excipient.

In another preferred embodiment, the formulation is a liquid formulation.

In another preferred embodiment, the dosage form of the formulation is an injection.

In another preferred embodiment, the concentration of the CAR-T cells in the formulation is $1\times10^3$-$1\times10^8$ cells/ml, preferably $1\times10^4$-$1\times10^7$ cells/ml.

In another preferred embodiment, the pharmaceutical composition further comprises a second active ingredient against tumor, preferably comprises a second antibody, or a chemotherapeutic agent.

In another preferred embodiment, the chemotherapeutic agent is selected from the group consisting of docetaxel, carboplatin, and a combination thereof.

In the seventh aspect of the present invention, it provides a use of the chimeric antigen receptor of the first aspect of the present invention, the nucleic acid molecule of the second aspect of the present invention, the vector of the third aspect of the present invention, or the immune cell of the fifth aspect of the present invention, or the formulation of the sixth aspect of the present invention, for the preparation of a medicament or formulation for the prevention and/or treatment of cancer or tumor.

In another preferred embodiment, the tumor is selected from the group consisting of a hematological tumor, a solid tumor, and a combination thereof.

In another preferred embodiment, the hematological tumor is selected from the group consisting of acute myeloid leukemia (AML), multiple myeloma (MM), chronic lymphocytic leukemia (CLL), acute lymphoblastic leukemia (ALL), diffuse large B-cell lymphoma (DLBCL), and a combination thereof.

In another preferred embodiment, the solid tumor is selected from the group consisting of gastric cancer, gastric cancer peritoneal metastasis, liver cancer, leukemia, kidney tumor, lung cancer, small intestine cancer, bone cancer, prostate cancer, colorectal cancer, breast cancer, colorectal cancer, cervical cancer, ovarian cancer, lymphoma, nasopharyngeal cancer, adrenal tumor, bladder tumor, non-small cell lung cancer (NSCLC), glioma, endometrial cancer, and a combination thereof.

In another preferred embodiment, the tumor is a CS1 and/or BCMA positive tumor.

In another preferred embodiment, the CS1 and/or BCMA positive tumor comprises multiple osteosarcoma.

In the eighth aspect of the present invention, it provides a kit for preparing the host cell of the fourth aspect or the engineered immune cell of the fifth aspect of the present invention, which comprises a container, and the nucleic acid molecule of the second aspect of the present invention or the vector of the third aspect of the present invention in the container.

In the ninth aspect of the present invention, it provides a method for preparing engineered immune cells expressing the CAR of the first aspect of the present invention, and the method comprises the following steps:

(a) providing immune cells to be modified; and (b) transferring the nucleic acid molecule of the second aspect of the present invention or the vector of the third aspect of the present invention into the immune cells to obtain the engineered immune cells.

In another preferred embodiment, the engineered immune cells are CAR-T cells or CAR-NK cells.

In another preferred embodiment, the method further comprises the step of performing functional and effective tests on the engineered immune cells obtained.

In the tenth aspect of the present invention, it provides a method of treating a disease, comprising administering an appropriate amount of the vector of the third aspect of the present invention, the immune cell of the fifth aspect of the present invention, or the formulation of the sixth aspect of the present invention to a subject in need of treatment.

In another preferred embodiment, the disease is a cancer or a tumor.

It should be understood that within the scope of the present invention, each technical features of the present invention described above and in the following (such as examples) may be combined with each other to form a new or preferred technical solution, which is not listed here due to space limitations.

DESCRIPTION OF THE DRAWINGS

FIG. 1 shows the structure of CAR. Wherein, The left side of the figure is the first generation CAR (no costimulatory domain), the middle is the second generation CAR (one costimulatory domain, CD28 or 4-BB), and the right is the third generation CAR (two or more costimulatory domains).

FIG. 2 shows the sequences of CS1 and BCMA antigens.

FIG. 3 shows the structure of the bispecific CS1-BCMA CAR construct. Wherein, the second generation CAR structure and the 4-1BB costimulatory domain were used.

FIG. 4 shows a diagram of the sequence of a preferred CAR construct in the present invention.

FIG. 6 shows the expression and killing of CS1-BCMA-CAR-T cells. FIG. 6A shows CHO-BCMA, CHO-CS1 and Hela-CS1 cells stably express BCMA and CS1 antigens. Wherein, FACS detection was performed with isotype and BCMA antibody on CHO-BCMA cells, and FACS detection was performed with CS1 antibody on CHO-CS1 cells and Hela-CS1 cells. The isotype Ab was labeled blue. CS1 and BCMA Abs were labeled red. FIG. 6B shows that CS1-BCMA-CAR-T cells specifically kill CHO-CS1 cells. Cytotoxicity test showed that CS1-BCMA-CAR-T cells killed CHO-CS1 cells. Wherein, BCMA-CAR-T cells and Mock CAR-T cells were used as negative controls.

FIG. 10 shows that CS1-BCMA-CAR-T cells secrete high levels of IFN-γ against CHO-CS1 and CHO-BCMA target cells, and do not secrete IFN-γ against CHO cells. *$p<0.05$, according to Student's t test, CS1-BCMA-CAR-T cells are compared with Mock CAR-T cells.

FIG. 12 shows the results of CAR+ cells derived from three different donors detected by FACS with mouse FAB and biotinylated recombinant BCMA protein. Wherein, FIG. 12A shows the FACS detection results of donor #57; FIG. 12B shows the FACS detection results of donor #890; FIG. 12C shows the FACS detection results of donor #999.

FIG. 13 shows the RTCA analysis results of CS1-BCMA-CAR-T cells from three donors. Wherein, FIG. 13A shows the RTCA analysis results of donor #57;

FIG. 13B shows the RTCA analysis results of donor #890; FIG. 13C shows the RTCA analysis results of donor #999.

FIG. 14 shows the IFN-γ secretion of CS1-BCMA CAR-T cells derived from three donors. Wherein, FIG. 14A shows the IFN-γ secretion of donor #57(A); FIG. 14B shows the IFN-γ secretion of donor #890; FIG. 14C shows the IFN-γ secretion of donor #999.

DETAILED DESCRIPTION

Figure 5:
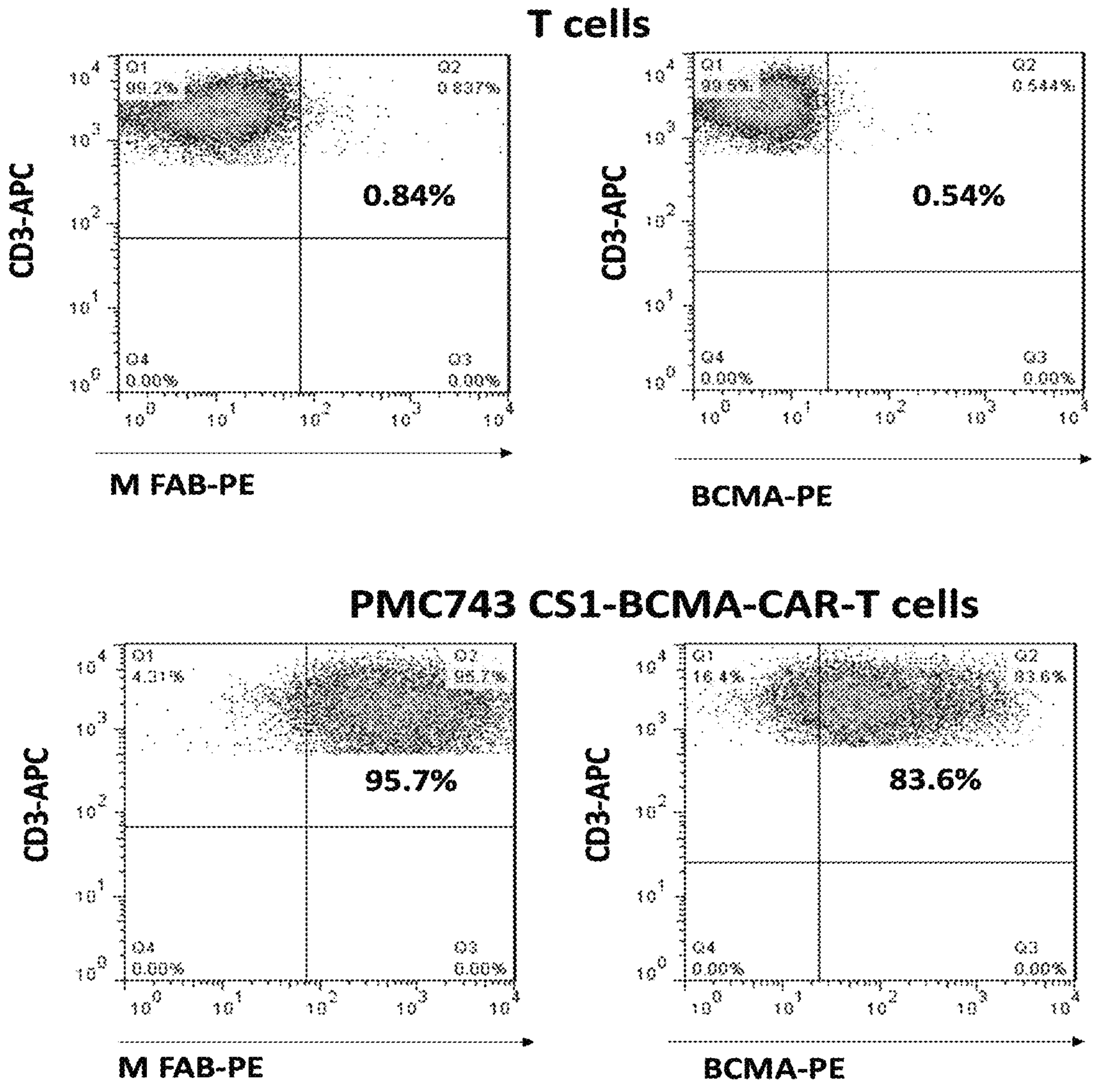
FIG. 5 shows the percentage of CAR-positive cells. Wherein, the mouse FAB antibody and biotin-PE labeled BCMA recombinant protein were used to detect CAR+ cells by FACS, and >95% of CAR+ cells were detected by FAB antibody, and >80% of BCMA+ ScFv cells were detected by BCMA protein.

After extensive and intensive research, the inventors surprisingly discovered a bispecific CAR targeting CS1 and BCMA for the first time. The bispecific CAR comprises a CS1 scFv and a BCMA scFv, as well as a 4-1BB costimulatory domain and a CD3 activating domain. Experiments show that the bispecific CAR-T cells of the present invention have a significant killing effect on CS1 positive target cells and BCMA positive target cells, can secrete IFN-γ against target cells, and significantly inhibit the growth of RPMI8226 xenograft tumors in vivo. On this basis, the present invention has been completed.

Term

In order to make this disclosure easier to understand, certain terms are first defined. As used in this application, unless expressly provided otherwise herein, each of the following terms shall have the meanings given below. Additional definitions are set forth throughout the application.

The term "about" may refer to a value or composition within the acceptable error range of a particular value or composition as determined by those skilled in the art, which will depend in part on how the value or composition is measured or determined.

The term "administration" refers to the physical introduction of a product of the present invention into a subject using any of a variety of methods and delivery systems known to those skilled in the art, including intravenous, intramuscular, subcutaneous, intraperitoneal, spinal or other parenteral routes of administration, such as by injection or infusion.

The term "antibody" (Ab) should include, but not be limited to, an immunoglobulin, which specifically binds an antigen and comprises at least two heavy (H) and two light (L) chains interconnected by disulfide bonds, or an antigen-binding moiety thereof. Each H chain contains a heavy chain variable region (abbreviated as VH herein) and a heavy chain constant region. The heavy chain constant region contains three constant domains CH1, CH2 and CH3. Each light chain contains a light chain variable region (abbreviated as VL herein) and a light chain constant region. The light chain constant region contains a constant domain CL. The VH and VL regions can be further subdivided into hypervariable regions called complementarity determining regions (CDRs), which are scattered with more conservative regions called framework regions (FRs). Each VH and VL comprises three CDRs and four FRs, which are arranged in the following order from the amino terminus to the carboxyl terminus: FR1, CDR1, FR2, CDR2, FR3, CDR3, FR4. The variable regions of the heavy and light chains contain binding domains that interact with the antigen.

It should be understood that the amino acid name herein adopts the internationally accepted single-English letter identification, and the corresponding amino acid names abbreviated in three English letters are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

CS1 and BCMA Antigens

CS1 (SLAM family member 7, CD319) and BCMA (tumor necrosis factor receptor superfamily member 17) proteins are commonly overexpressed in multiple myeloma.

Based on their high percentage of expression in multiple myeloma, both targets are used for CAR-T cell therapy.

FIG. 2 shows the amino acid sequence of CS1 antigen (SEQ ID NO: 12) and the amino acid sequence of BCMA antigen (SEQ ID NO: 13), in which the extracellular domain of BCMA (1-54 aa) and the extracellular domain of CS1 (23-226 aa) are underlined.

Chimeric Antigen Receptor (CAR)

As used herein, the terms "CS1-BCMA-CAR", "bispecific CAR", and "CS1-BCMA bispecific CAR" have the same meaning, referring to the CAR targeting CS1 and BCMA provided in the first aspect of the present invention. Specifically, the CS1-BCMA bispecific CAR of the present invention consists of two scFv, a 4-1BB costimulatory domain and a CD3 activating domain (FIG. 3). For BCMA scFv contained in bispecific CAR, the BCMA scFv derived from clone 4C8 (R. Berahovich, et al., CAR-T Cells Based on Novel BCMA Monoclonal Antibody Block Multiple Myeloma Cell Growth. Cancers (Basel) 10 (2018).) is used, and the amino acid sequences of which are shown in SEQ ID NOs: 4 and 5. For CS1 scFv contained in bispecific CAR, the CSI antibody 7A8D5 from Promab is used, and the amino acid sequences of which are shown in SEQ ID NOs: 1 and 2. Experiments show that the CS1 scFv also works well against CS1 positive target cells in the form of mono-specific CAR.

The design of CARs has gone through the following process: the first generation of CAR has only one intracellular signal component, CD3ζ or FcγRI molecule. Since there is only one activating domain in the cell, it can only cause short-term T cell proliferation and less cytokine secretion, but cannot provide long-term T cell proliferation signal and continuous in vivo anti-tumor effect, so it has not achieved good clinical efficacy. In the second generation CAR, a costimulatory molecule, such as CD28, 4-1BB, OX40 and ICOS, is introduced on the basis of the original structure. Compared with the first generation CARs, the function is greatly improved, further enhancing the persistence of CAR-T cells and the killing ability against tumor cells. On the basis of the second generation CARs, some new immune costimulatory molecules such as CD27 and CD134 are connected in tandem to develope the third and fourth generation CARs.

The chimeric antigen receptor (CAR) of the present invention is a second-generation CAR, including an extracellular domain, a transmembrane domain, and an intracellular domain. The extracellular domain includes a target-specific binding element (also called antigen binding domain). The intracellular domain includes a costimulatory signal transduction region and a zeta chain part. The costimulatory signal transduction region refers to a part of intracellular domain including costimulatory molecules. The costimulatory molecules are the cell surface molecules needed for the effective response of lymphocytes to antigens, not antigen receptors or their ligands.

A linker may be incorporated between the extracellular and transmembrane domains of the CAR, or between the cytoplasmic and transmembrane domains of the CAR. As used herein, the term "linker" generally refers to any oligopeptide or polypeptide that plays the role of connecting the transmembrane domain to the extracellular domain or cytoplasmic domain of the polypeptide chain. The linker may comprise 0 to 300 amino acids, preferably 2 to 100 amino acids and most preferably 3 to 50 amino acids.

In a preferred embodiment of the present invention, the extracellular domain of CAR provided by the present invention comprises an antigen binding domain (CS1-BCMA scFv) targeting CS1 and BCMA. The CAR of the present invention, when expressed in T cells, is capable of antigen recognition based on antigen binding specificity. When it binds to its associated antigen, it affects tumor cells, causing tumor cells to not grow, be killed or be affected in other ways, and leading to the reduction or elimination of tumor burden of patients. The antigen binding domain is preferably fused with one or more intracellular domains from the costimulatory molecules and the zeta chain.

As used herein, "antigen-binding domain" and "single-chain antibody fragment" both refer to a Fab fragment, a Fab' fragment, a $F(ab')_2$ fragment, or a single Fv fragment with antigen-binding activity. Fv antibody contains antibody heavy chain variable region and light chain variable region, but no constant region, and has the smallest antibody fragment of all antigen binding sites. In general, Fv antibody further contains a polypeptide linker between the VH and VL domains and is capable of forming the structure required for antigen binding. The antigen binding domain is usually a scFv (single-chain variable fragment). The size of scFv is generally ⅙ of an intact antibody. The single-chain antibody is preferably an amino acid chain sequence encoded by a nucleotide chain.

For the hinge region and the transmembrane region (transmembrane domain), the CAR can be designed to include a transmembrane domain fused to the extracellular domain of the CAR. In one embodiment, a transmembrane domain naturally associated with one of the domains in the CAR is used. In some examples, the transmembrane domain may be selected, or modified by amino acid substitution, to avoid binding such domains to transmembrane domains of the same or different surface membrane proteins, thereby minimizing interaction with other members of the receptor complex.

Specifically, in a preferred embodiment of the present invention, in order to improve the viability of CAR-T cells in the tumor microenvironment, a second-generation CAR vector targeting CS1 and BCMA is constructed using 4-1BB as the costimulatory domain, which sequentially includes the single-chain antibody sequence of humanized CS1 antibody, the single-chain antibody sequence of humanized BCMA antibody, the intracellular region sequence, the intracellular region sequence of human 4-1BB, and human CD3ζ sequence.

In a preferred embodiment of the present invention, the chimeric antigen receptor of the present invention is shown in FIG. 4.

Further, the CS1-BCMA-CAR sequence is placed downstream of the MNDU3 promoter of the second generation lentiviral construct with kanamycin resistance gene to construct a lentiviral vector expressing CS1-BCMA-CAR. 293 T cells are used to produce lentivirus and transduce T cells to prepare CS1-BCMA-CAR-T cells. For specific methods, please refer to the General Methods section.

Vector

The nucleic acid sequence encoding the desired molecule may be obtained using recombination methods known in the art, such as, for example, by screening a library from cells expressing the gene, by deriving the gene from a vector known to include the gene, or by direct isolation from cells and tissues containing the gene using standard techniques. Optionally, the gene of interest may be synthesized.

The present invention also provides a vector in which the expression cassette of the present invention is inserted. Vectors derived from retroviruses such as lentiviruses are suitable tools for long-term gene transfer because they allow long-term, stable integration of transgenes and their proliferation in daughter cells. Lentiviral vectors have advantages over vectors derived from carcinogenic retroviruses such as murine leukemia viruses because they can transduce non-proliferative cells, such as hepatocytes. They also have the advantage of low immunogenicity.

In brief summary, the expression cassette or nucleic acid sequence of the present invention is usually operably linked to the promoter and incorporated into the expression vector. The vector is suitable for replication and integration in eukaryotic cells. A typical cloning vector contains a transcription and translation terminator, an initial sequence, and a promoter that can be used to regulate expression of the desired nucleic acid sequences.

The expression construct of the present invention can also be used for nucleic acid immunization and gene therapy by using the standard gene delivery scheme. Methods of gene delivery are known in the art. See, for example, U.S. Pat. Nos. 5,399,346, 5,580,859, 5,589,466, which are incorporated herein by reference in their entirety. In another embodiment, the present invention provides a gene therapy vector.

The nucleic acid can be cloned into many types of vectors. For example, the nucleic acid may be cloned into such vectors, including, but not limited to, plasmids, phage derivatives, animal viruses, and cosmids. Specific vectors of interest include expression vectors, replication vectors, probe generation vectors, and sequencing vectors.

Further, the expression vector may be provided to the cell in the form of a viral vector. Viral vector technology is well known in the art and is described in, for example, Sambrook et al. (2001, Molecular Cloning: A Laboratory Manual, Cold Spring Harbor Laboratory, New York) and other manuals of virology and molecular biology. Viruses that may be used as vectors include, but are not limited to, retroviruses, adenoviruses, adeno-associated viruses, herpes viruses, and lentiviruses. Typically, a suitable vector comprises a replication origin, a promoter sequence, a convenient restriction enzyme site, and one or more selectable markers operative in at least one organism (e.g., WO01/96584; WO01/29058; and U.S. Pat. No. 6,326,193).

A number of virus-based systems have been developed for the transfer of genes into mammalian cells. For example, retroviruses provide a convenient platform for gene delivery systems. Selective genes can be inserted into vectors and packaged into retroviral particles using techniques known in the art. The recombinant virus can then be isolated and delivered to the subject cells in vivo or ex vivo. Many retroviral systems are known in the art. In some embodiments, an adenoviral vector is used. Many adenoviral vectors are known in the art. In one embodiment, a lentiviral vector is used.

Additional promoter elements, such as enhancers, can regulate the frequency of transcription initiation. Typically, these are located in the region 30-110 bp upstream of the start site, although it has recently been shown that many promoters also contain functional elements downstream of the start site. The spacing between promoter elements is often flexible so that when the element is inverted or moved relative to another one, the promoter function is maintained. In the thymidine kinase (tk) promoter, the separation between the promoter elements can be increased by 50 bp, before the activity begins to decline. Depending on the promoter, it is shown that a single element can act cooperatively or independently to initiate transcription.

An example of a suitable promoter is the immediate early cytomegalovirus (CMV) promoter sequence. The promoter sequence is a strongly constitutive promoter sequence capable of driving high-level expression of any polynucleotide sequence operably linked to it. Another example of a suitable promoter is the elongation growth factor-1α (EF-1α). However, other constitutive promoter sequences can also be used, including but not limited to early promoter of simian virus 40 (SV40), mouse breast tumor virus (MMTV), human immunodeficiency virus (HIV) long-terminal repeat (LTR) promoter, MoMuLV promoter, avian leukemia virus promoter, immediate early promoter of Epstein-Barr virus, Ruth's sarcoma virus promoter, and human gene promoter, such as, but not limited to, an actin promoter, a myosin promoter, a heme promoter, and a creatine kinase promoter. Further, the present invention should not be limited to the use of constitutive promoters. Inducible promoters are also considered as part of the present invention. The use of inducible promoters provides a molecular switch that can turn on expression of a polynucleotide sequence operably linked to an inducible promoter when such expression is desired, or turn off expression when the expression is undesirable. Examples of inducible promoters include, but are not limited to, a metallothionein promoter, a glucocorticoid promoter, a progesterone promoter, and a tetracycline promoter.

In order to evaluate the expression of the CAR polypeptide or part thereof, the expression vector introduced into the cell may also contain either or both of the selectable marker genes or reporter genes in order to identify and select the expression cells from the cell population seeking to be transfected or infected by the viral vector. In other aspects, selectable markers can be carried on a single piece of DNA and used in co-transfection procedures. Both selectable markers and reporter genes can be flanked with appropriate regulatory sequences to be able to be expressed in host cells. Useful selectable markers include, for example, antibiotic resistance genes, such as neo, etc.

Reporter genes are used to identify potentially transfected cells and to evaluate the functionality of regulatory sequences. Typically, the reporter gene is the following gene: it is not present in or expressed by the recipient organism or tissue, and it encodes a polypeptide of which the expression is clearly represented by some easily detectable properties such as enzyme activity. After DNA has been introduced into the receptor cells, the expression of the reporter gene is determined at the right time. Suitable reporter genes may include genes encoding luciferase, β-galactosidase, chloramphenicol acetyltransferase, secretory alkaline phosphatase, or green fluorescent protein (e.g., Ui-Tei et al., 2000FEBS Letters 479:79-82). Suitable expression systems are well known and can be prepared using known techniques or commercially available. In general, a construct with a minimum of 5 flanking regions that show the highest level of reporter expression are identified as a promoter. Such promoter region can be linked to a reporter gene and used to evaluate the ability of a reagent to regulate promoter-driven transcription.

Methods of introducing genes into cells and expressing genes into cells are known in the art. In the content of the expression vector, the vector can be easily introduced into the host cell, for example, mammalian, bacterial, yeast or insect cells, by any method in the art. For example, the expression vector can be transferred into the host cell by physical, chemical or biological means.

Physical methods for introducing polynucleotides into host cells include calcium phosphate precipitation, lipid transfection, particle bombardment, microinjection, electroporation, etc. Methods of producing cells including vectors and/or exogenous nucleic acids are well known in the art. See, for example, Sambrook, et al. (2001, Molecular Cloning: A Laboratory Manual, Cold Spring Harbor Laboratory, New York). A preferred method for introducing polynucleotides into host cells is calcium phosphate transfection.

Biological methods of introducing polynucleotides of interest into host cells include the use of DNA and RNA vectors. Viral vectors, especially retroviral vectors, have become the most widely used method for inserting genes into mammalian cells such as human cells. Other viral vectors may be derived from lentivirus, poxvirus, herpes simplex virus I, adenovirus and adeno-associated virus, etc. See, for example, U.S. Pat. Nos. 5,350,674 and 5,585,362.

Chemical means of introducing polynucleotides into host cells include colloidal dispersion systems, such as macromolecular complexes, nanocapsules, microspheres, beads; and lipid-based systems, including oil-in-water emulsions, micelles, mixed micelles, and liposomes. An exemplary colloidal system used as an in vitro and in vivo delivery vehicle is a liposome (e.g., an artificial membrane capsule).

In the case of using a non-viral delivery system, the exemplary delivery tool is liposome. The use of lipid preparations is considered to introduce nucleic acids into host cells (in vitro, ex vivo or in vivo). In another aspect, the nucleic acid may be associated with lipids. The nucleic acid associated with lipids may be encapsulated into the aqueous interior of the liposome, scattered in the lipid bilayer of the liposome, attached to the liposome by a connecting molecule associated with both the liposome and the oligonucleotide, trapped in the liposome, compounded with the liposome, dispersed in a solution containing the lipid, mixed with the lipid, combined with the lipid, contained in the lipid as a suspension, contained in the micelle or compounded with the micelle, or otherwise associated with lipids. Lipids, lipid/DNA or lipid/expression vectors associated with the composition are not limited to any specific structure in solution. For example, they may exist in bilayer structures as micelles or have "collapsed" structures. They may also be simply dispersed in solution, possibly forming aggregates of uneven size or shape. Lipids are fatty substances, which may be naturally occurring or synthesized lipids. For example, lipids include fat droplets that occur naturally in the cytoplasm and in compounds containing long-chain aliphatic hydrocarbons and their derivatives, such as fatty acids, alcohols, amines, amino alcohols and aldehydes.

In a preferred embodiment of the present invention, the vector is a lentiviral vector.

Formulation

The present invention provides a formulation comprising the CAR-T cell of the present invention, and a pharmaceutically acceptable carrier, diluent or excipient. In one embodiment, the formulation is a liquid formulation. Preferably, the formulation is an injection. Preferably, the concentration of the CAR-T cells in the formulation is $1\times10^3$-$1\times10^8$ cells/ml, more preferably $1\times10^4$-$1\times10^7$ cells/ml.

In one embodiment, the formulation may include buffers such as neutral buffered saline, sulfate buffered saline, etc.; carbohydrates such as glucose, mannose, sucrose or glucan, mannitol; proteins; polypeptides or amino acids such as glycine; antioxidants; chelating agents such as EDTA or glutathione; adjuvants (e.g., aluminum hydroxide); and preservatives. The formulations of the present invention are preferably formulated for intravenous administration.

Therapeutic Use

The present invention includes therapeutic use of cells (e.g., T cells) transduced with a lentiviral vector (LV) encoding the expression cassette of the present invention. Transducted T cells can target tumor cell markers CS1 and BCMA, synergistically activate T cells and cause T cell immune response, thus significantly improving the killing efficiency against tumor cells.

Accordingly, the present invention also provides a method of stimulating a T cell-mediated immune response to a target cell population or tissue of a mammal, which comprises the step of administering to a mammal the CAR-T cells of the present invention.

In one embodiment, the present invention includes a type of cell therapy in which autologous T cells from a patient (or heterologous ones from a donor) are isolated, activated and genetically modified to produce CAR-T cells, and subsequently injected into the same patient. In this way, the probability of graft-versus-host disease is extremely low, and the antigen is recognized by T cells in a manner without MHC restriction. In addition, one CAR-T can treat all cancers that express the antigen. Unlike antibody therapy, CAR-T cells can replicate in vivo, resulting in long-term persistence that can lead to sustained tumor control.

In one embodiment, the CAR-T cells of the present invention can undergo stable in vivo T cell expansion and can last an extended amount of time. In addition, the CAR-mediated immune response can be part of an adoptive immunotherapy step in which CAR-modified T cells induce an immune response specific to the antigen-binding domain in the CAR. For example, anti-CS1 and BCMA CAR-T cells elicit a specific immune response against CS1 and/or BCMA-positive cells.

Although the data disclosed herein specifically disclose lentiviral vectors that include the MNDU3 promoter, CS1-BCMA scFv, 4-1BB intracellular region, and CD3ζ signaling domain, the present invention should be interpreted to include any number of changes to each of the construct components.

Treatable cancers include tumors that have not been vascularized or have basically not been vascularized, and tumors that have been vascularized. The cancers may include non-solid tumors (such as hematological tumors, e.g., leukemia and lymphoma) or may include solid tumors. The types of cancer treated with the CAR of the present invention include, but are not limited to, carcinomas, blastocytomas, and sarcomas, and certain leukemic or lymphoid malignancies, benign and malignant tumors, and malignant tumors, such as sarcomas, carcinomas, and melanoma. It also includes adult tumors/cancers and pediatric tumors/cancers.

Hematological cancers are cancers of the blood or bone marrow. Examples of hematological (or haematogenic) cancers include leukemia, including acute leukemia (such as acute lymphocytic leukemia, acute myeloid leukemia, acute myelogenous leukemia and myeloblastic, premyelocytic, granulo-monocytic, monocytic and erythroleukemia), chronic leukemia (such as chronic myeloid (granulocytic) leukemia, chronic myelogenous leukemia and chronic lymphocytic leukemia), polycythemia vera, lymphoma, Hodgkin's disease, non-Hodgkin's lymphoma (painless and high-grade forms), multiple myeloma, Waldenstrom's macroglobulinemia, heavy chain disease, myelodysplastic syndrome, hairy cell leukemia and spinal cord dysplasia.

A solid tumor is an abnormal mass of tissue that usually does not contain a cyst or fluid area. A solid tumor may be benign or malignant. Different types of solid tumors are named after the cell types that form them (such as sarcomas, carcinomas, and lymphomas). Examples of solid tumors such as sarcomas and carcinomas include fibrosarcoma, mucinous sarcoma, liposarcoma mesothelioma, lymphoid malignant tumor, pancreatic carcinoma and ovarian carcinoma.

In a preferred embodiment, the treatable cancer is a CS1 and/or BCMA positive tumor, such as multiple osteosarcoma, etc.

The CAR-modified T cells of the present invention can also be used as a vaccine type for ex vivo immunization and/or in vivo therapy of mammals. Preferably, the mammal is a human.

For ex vivo immunization, at least one of the following occurs in vitro before the cells are administered into mammals: i) expanding the cells, ii) introducing the nucleic acid encoding a CAR into the cells, and/or iii) cryopreservation of the cells.

The ex vivo procedure is well known in the art and is discussed more fully below. In brief, cells are isolated from mammals (preferably humans) and genetically modified (i.e., transduced or transfected in vitro) with a vector expressing the CAR disclosed herein. CAR-modified cells can be administered to mammalian recipients to provide therapeutic benefits. The mammalian recipient may be a human, and CAR-modified cells may be autologous relative to the recipient. Optionally, the cells may be allogeneic, syngeneic or xenogeneic relative to the recipient.

In addition to the use of cell-based vaccines in terms of ex vivo immunization, the present invention also provides compositions and methods for in vivo immunization to induce an immune response against an antigen in a patient.

The present invention provides a method of treating a tumor comprising administering to a subject in need thereof a therapeutically effective amount of the CAR-modified T cells of the present invention.

The CAR-modified T cells of the present invention may be administered alone or as a pharmaceutical composition in combination with a diluent and/or with other components such as IL-2, IL-17 or other cytokines or cell populations. Briefly, the pharmaceutical composition of the present invention may comprise a population of target cells as described herein in combination with one or more pharmaceutically or physiologically acceptable carriers, diluents or excipients. Such compositions may include buffers such as neutral buffered saline, sulfate buffered saline, etc.; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives. The composition of the present invention is preferably formulated for intravenous administration.

The pharmaceutical composition of the present invention may be administered in a manner suitable for the disease to be treated (or prevented). The number and frequency of administration will be determined by such factors as the patient's condition, and the type and severity of the patient's disease, although the appropriate dose may be determined by clinical trials.

When "immunologically effective amount", "anti-tumor effective amount", "tumor-suppressive effective amount" or "therapeutic amount" is indicated, the precise amount of the composition of the present invention to be administered may be determined by a physician taking into account individual differences in age, weight, tumor size, degree of infection or metastasis, and condition of the patient (subject). It may be generally noted that the pharmaceutical composition comprising T cells described herein may be administered at a dose of $10^4$ to $10^9$ cells/kg body weight, preferably at a dose of $10^5$ to $10^6$ cells/kg body weight (including all integer values in those ranges). T cell compositions may also be administered multiple times at these doses. Cells can be administered by using injection techniques well known in immunotherapy (see e.g., Rosenberg et al., New Eng. J. of Med. 319:1676, 1988). The optimal dosage and treatment regimen for a specific patient can be easily determined by a skilled person in the medical field by monitoring the patient's signs of disease and adjusting the treatment accordingly.

The administration of the subject composition can be carried out in any convenient manner, including by spraying, injection, swallowing, infusion, implantation or transplantation. The compositions described herein may be administered to a patient subcutaneously, intradermally, intratumorally, intranodally, intraspinally, intramuscularly, by intravenous (i.v.) injection, or intraperitoneally. In one embodiment, the T cell composition of the present invention is administered to a patient by intradermal or subcutaneous injection. In another embodiment, the T cell composition of the present invention is preferably administered by i.v. injection. The composition of T cells can be injected directly into tumors, lymph nodes or infected sites.

In certain embodiments of the present invention, cells activated and expanded using the methods described herein or other methods known in the art to expand T cells to therapeutic levels are administered to the patient in combination with (e.g., before, simultaneously, or after) any number of relevant treatment forms, including but not limited to treatment with the following agents: the agents such as antiviral therapy, cidofovir and interleukin-2, cytarabine (also known as ARA-C) or natalizumab therapy in MS patients or efalizumab therapy in psoriasis patients or other therapy in PML patients. In further embodiments, the T cells of the present invention may be used in combination with chemotherapy, radiation, immunosuppressive agents such as cyclosporin, azathioprine, methotrexate, mycophenolate and FK506, antibodies or other immunotherapeutic agents. In further embodiments, the cell composition of the present invention is administered to a patient in combination with (e.g., before, simultaneously, or after) bone marrow transplantation, the use of a chemotherapeutic agent such as fludarabine, external beam radiotherapy (XRT), cyclophosphamide. For example, in one embodiment, a subject may undergo a standard treatment of high-dose chemotherapy followed by peripheral blood stem cell transplantation. In some embodiments, after transplantation, the subject receives an infusion of the expanded immune cells of the present invention. In an additional embodiment, the expanded cells are administered before or after surgery.

The dose of the above treatment administered to the patient will vary with the precise attributes of the treated disorder and the recipient of the treatment. The proportion of doses administered to humans may be implemented according to practices accepted in the field. Typically, $1\times10^6$ to $1\times10^{10}$ modified T cells (e.g., CAR-T cells) of the present invention may be administered to the patient by, for example, intravenous reinfusion per treatment or per course of treatment.

The Main Advantages of the Present Invention Include (a) The bispecific CAR-T cells of the present invention have a significant killing effect on CS1 positive target cells and BCMA positive target cells.

(B) The bispecific CAR-T cells of the present invention secrete IFN-γ against CS1 positive target cells and BCMA positive target cells.

(c) The bispecific CAR-T cells of the present invention can significantly inhibit the growth of RPMI8226 xenograft tumors in vivo.

The present invention is further explained below in conjunction with specific example. It should be understood that these examples are only for illustrating the present invention and not intend to limit the scope of the present invention. The experimental methods of which the conditions are not specifically indicated in the following examples are usually in accordance with conventional conditions such as those described in Sambrook et al., Molecular Cloning: A Laboratory Manual (New York: Cold Spring Harbor Laboratory Press, 1989), or according to the conditions recommended by the manufacturer. Unless otherwise stated, percentages and parts are calculated by weight.

General Materials and Methods

1. Isolation of Peripheral Blood Mononuclear Cells (PBMCs) from Whole Blood

Whole blood collected from single or multiple donors (depending on the amount of blood required) (Stanford Hospital Blood Center, Stanford, California) was added to a 10 mL heparin vacuum container (purchased from Becton Dickinson). In a 50 ml conical centrifuge tube (PBS, pH 7.4, $Ca2^+/Mg2^+$ free), about 10 ml of anticoagulant whole blood was mixed with sterile phosphate buffer saline (PBS) for a total volume of 20 ml. The cell layer containing peripheral blood mononuclear cells (PBMCs) on the diluted plasma/Ficoll interface was carefully sucked to avoid inhaling any Ficoll, washed twice with PBS, and centrifuged at 200×g for 10 minutes at room temperature. The cells were counted with a blood cell counter. PBMCs were washed once with CAR-T medium (AIM V-AlbuMAX (BSA) (Life Technologies) which contained 5% AB serum and 1.25 ug/mL amphotericin B (Gemini Bioproducts, Woodland, CA), 100 U/mL penicillin, and 100 ug/mL streptomycin). Cells were directly used in subsequent experiments or cryopreserved at −80° C.

2. T Cell Activation

The isolated cells (washed with 1×PBS (pH 7.4), $Ca^{2+}/Mg^{2+}$ free) were washed once with CAR-T medium (AIM V-AlbuMAX (BSA) (Life Technologies) without addition of human interleukin-2 (huIL-2) (Invitrogen). CAR-T medium contained 5% AB serum and 1.25 ug/mL amphotericin B (Gemini Bioproducts, Woodland, CA), 100 U/mL penicillin, and 100 ug/mL streptomycin). The cell concentration was $5\times10^5$ cells/ml. The cells were re-suspended in CAR-T medium containing 300 U/mL huIL2, and the final concentration was $5\times10^5$ cells/mL. PBMCs were activated at a CD3-CD28 magnetic bead to cell ratio of 1:1.

3. T Cell Transduction and Expansion

After PBMC activation, the cells were incubated at 37° C., 5% $CO_2$ for 24 hours. Each well contained $1\times10^6$ cells, and $5\times10^6$ lentiviruses and 2 µL/mL of Transplus medium (Alstem, Richmond, California) were added (final dilution was 1:500). Cells were incubated for another 24 hours before the viruses were added repeatedly. Cells were cultured for 12-14 days in the persistence of fresh medium containing 300 U/mL IL-2 (the total incubation time depends on the final number of CAR-T cells required). The cell concentration was analyzed every 2-3 days, and the culture medium was added to dilute the cell suspension to $1\times10^6$ cells/mL.

3. FACS Detection of CAR Positive Cells

Cells were washed and suspended in FACS buffer (phosphate buffer saline (PBS) containing 0.1% sodium azide and 0.4% BSA). Cells were divided into aliquots ($1\times10^6$ cells). Fc receptors were blocked on ice with standard goat IgG (Life Technologies) for 10 minutes. Biotin-labeled polyclonal goat anti-mouse F(ab)2 antibody (Life Technologies) was used to detect CS1. BCMA-biotin-labeled recombinant protein was used to detect BCMA+ CAR cells. Biotin-labeled normal polyclonal goat IgG antibody (Life Technologies) was used as an isotype control. (1:200 dilution, reaction volume was 100 µl). Cells were incubated at 4° C. for 25 minutes and washed once with FACS buffer, then suspended in FACS buffer. Each tube was added with 100 µl 1:1000 diluted standard mouse IgG (Invitrogen) for blockade and incubated on ice for 10 minutes. The cells were then washed with FACS buffer and resuspended in 100 µl FACS buffer. Cells were then stained with phycoerythrin (PE)- labeled streptavidin (BD Pharmingen, San Diego, CA) and allophycocyanin (APC)-labeled CD3 (eBiocience, San Diego, CA).

4. Cytotoxicity Assay (Real-Time Cytotoxicity Assay)

The cytotoxicity assay was performed according to the manufacturer's operating guidelines using ACEA.

5. ELISA

IFN-γ cytokines were detected using ELISA kits, and the experiment was carried out according to the manufacturer's operating guidelines.

Example 1 CS1-BCMA-CAR-T Cells Express CS1 ScFv and BCMA scFv

The bispecific CS1-BCMA scFv fragment, 41BB costimulatory domain and CD3 zeta activating domain were inserted into CAR, and the CAR lentiviruses were transduced into T cells. The results show that CS1-BCMA-CAR cells are effectively expanded in vitro.

CAR containing no scFv and TF tags was constructed using the same method, named Mock CAR, and used as a negative control in cytotoxicity and cytokine assays.

CS1-BCMA-CAR positive cells were detected by FACS using mouse FAB antibody and biotin-labeled BCMA recombinant protein.

The results are shown in FIG. 5. The MNDU3 promoter was used for CAR-expressing lentivirus construction, and a high percentage of CAR-positive cells were in the cell transduction products.

The CAR-positive cells obtained in this example were named PMC743 and used in subsequent experiments.

Example 2 CS1-BCMA-CAR-T Cells Kill CHO-CS1 Cells and Hela-CS1 Cells

CS1-BCMA CAR-T cells (PMC743) were co-incubated with CHO-CS1 cells, Hela-CS1 cells (CS1 positive, CS1 antigen stably transfected cells), and CHO cells (CS1 negative), respectively. BCMA-41BB-CD3-CAR-T cells (PMC744) and Mock CAR-T cells were used as controls. The ratios of effect cells to target cells (E:T) preserved by cryopreservation were 20:1 and 40:1. The incubation time was 24 hours.

CHO-BCMA and CHO-CS1 staining with BCMA and CS1 antibodies is shown in FIG. 6A.

After 24 hours of co-incubation, XCelligence system was used to perform real-time cytotoxicity assay on CS1-BCMA-CAR-T cells and target cell lines.

The results show that CS1-BCMA-41BB-CD3 CAR-T cells (PMC743) can kill CHO-CS1 cells, while BCMA-41BB-CD3-CAR-T cells (PMC744) and Mock CAR-T cells (FIG. 6B) cannot kill CHO-CS1 cells.

Figure 7:
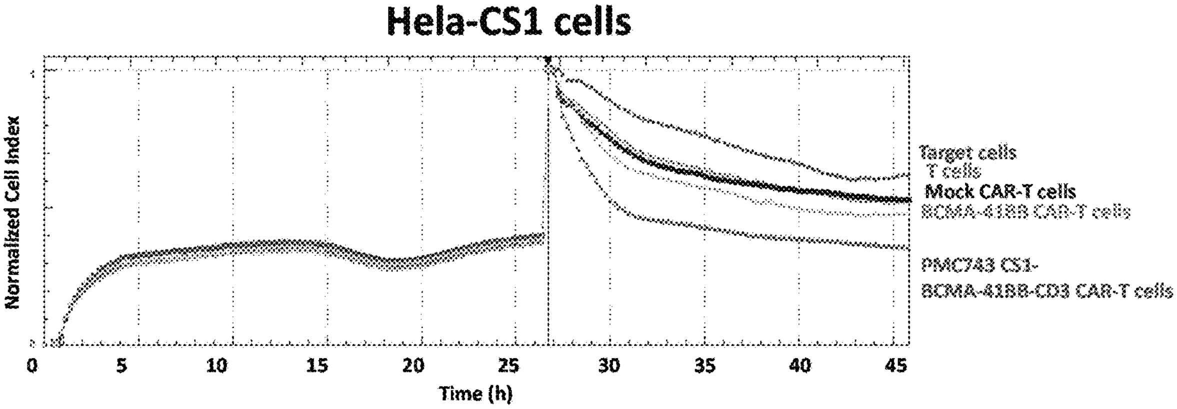
FIG. 7 shows that CS1-BCMA-CAR-T cells kill Hela-CS1 cells. Wherein, Mock CAR-T cells and BCMA-CAR-T cells were used as negative controls.

The same assay was performed with Hela-CS1. The results show that PMC743 can kill Hela-CS1 cells, while monospecific BCMA CAR-T cells can not kill Hela-CS1 cells (FIG. 7).

Example 3 CS1-BCMA-CAR-T Cells Specifically Kill CHO-BCMA Cells and Hela-BCMA Cells The same assay was performed with CHO and Hela cell lines stably expressing BCMA using a method similar to Example 2.

Figure 8:
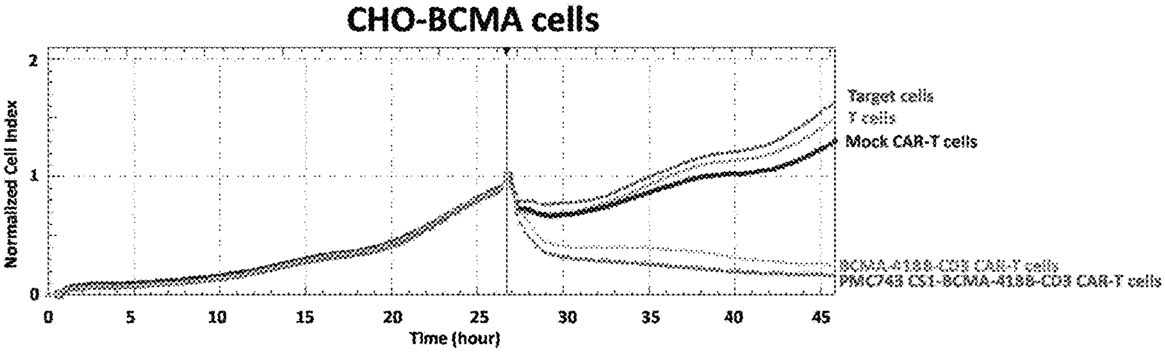
FIG. 8 shows that CS1-BCMA-CAR-T cells kill CHO-BCMA cells. Cytotoxicity test showed that CS1-BCMA-CAR-T cells killed CHO-BCMA target cells. Wherein, BCMA-CAR-T cells were used as positive control and Mock CAR-T cells were used as negative control.

The results show that, similar to BCMA-CAR-T cells, CS1-BCMA-CAR-T cells specifically kill BCMA positive target cells (FIG. 8).

Figure 9:
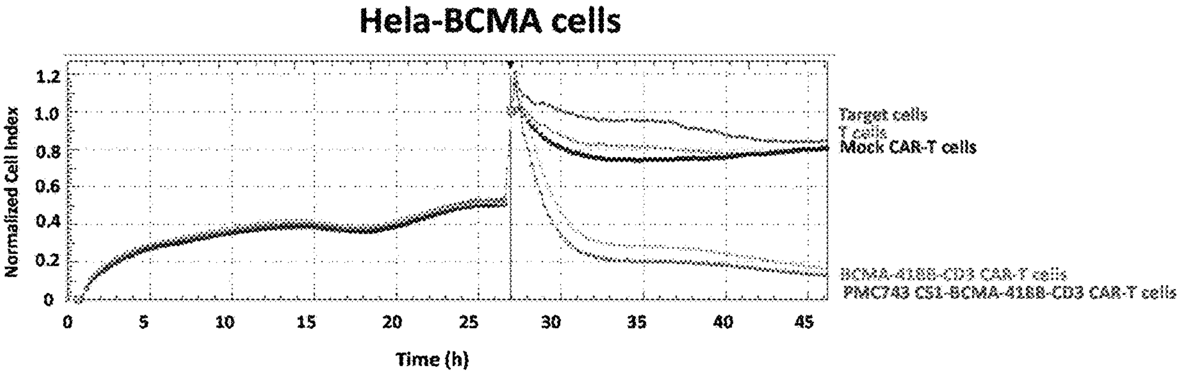
FIG. 9 shows that CS1-BCMA-CAR-T cells have a significantly stronger killing effect on Hela-BCMA cells than on Hela cells. Cytotoxicity test showed that CS1-BCMA-CAR-T cells killed Hela-BCMA target cells. BCMA-CAR-T cells were used as positive control and Mock CAR-T cells were used as negative control.

Hela-BCMA target cells (stably transducted with BCMA antigen) were used to perform detection. The results show that CS1-BCMA-CAR-T cells have high killing activity to them (FIG. 9).

Example 4 CS1-BCMA-CAR-T Cells Secret High Levels of IFN-γ Against CS1-Positive Cells CS1-BCMA-CAR-T cells were co-incubated with target cells, and the supernatant was collected. ELISA analysis was performed using Fisher's kit according to operating procedures.

Figure 11:
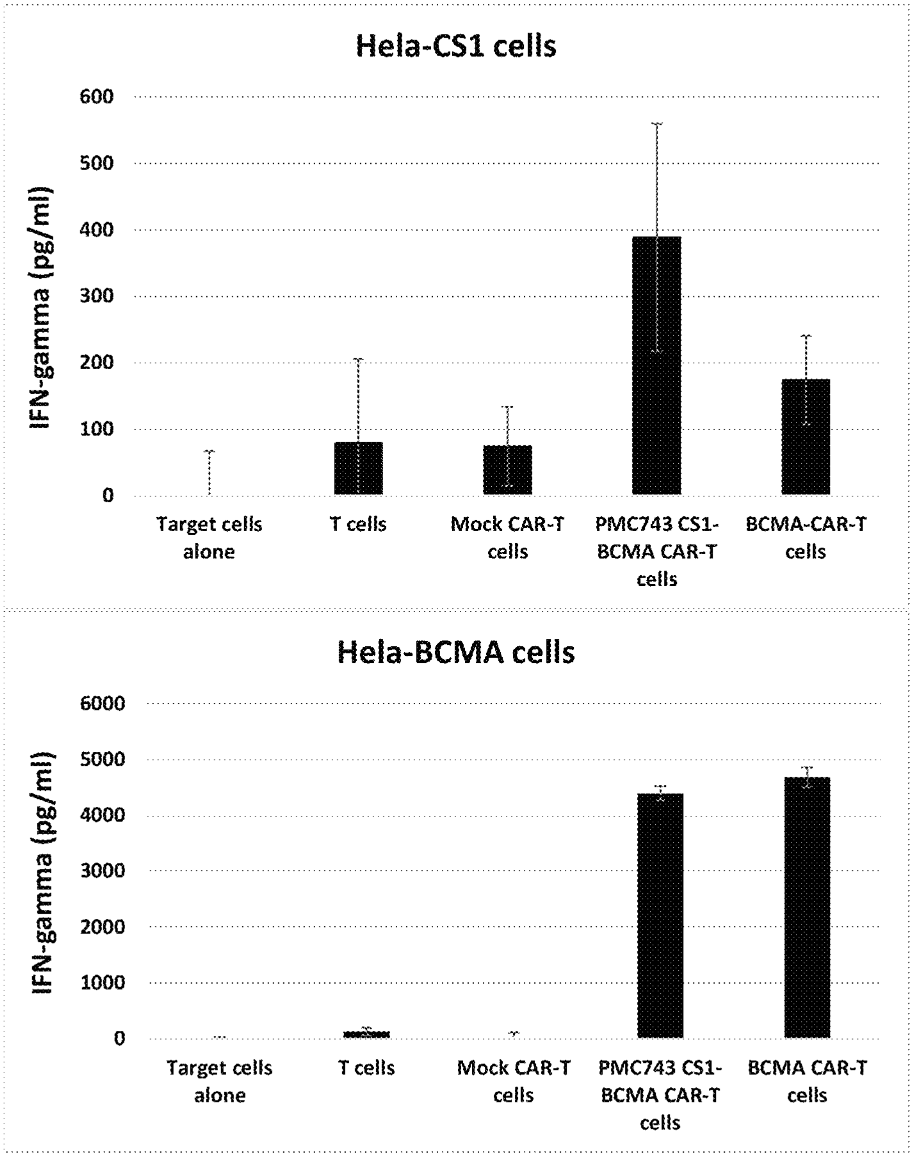
FIG. 11 shows that CS1-BCMA-CAR-T cells secrete IFN-γ against Hela-CS1 cells and Hela-BCMA cells. *$p<0.05$, according to Student's t test, CS1-BCMA-CAR-T cells are compared with Mock CAR-T cells.

The results show that after co-incubation of CS1-BCMA CAR-T cells with CHO-CS1 and CHO-BCMA (FIG. 10) and Hela-CS1 and Hela-BCMA cells (FIG. 11), high levels of IFN-γ secretion were detected. The above results show that CS1-BCMA-CAR-T cells can specifically target CS1 and BCMA positive target cells with high specificity.

Example 5 Preparation of CS1-BCMA-CAR-T Cells Using PBMCs from a Donor

Transduction of PMC743 CAR was performed using PBMCs from three donors, numbered #57, #890, and #999, respectively. Monospecific BCMA-CAR-T cells and CS1-CAR-T cells were used as controls.

Figure 12:
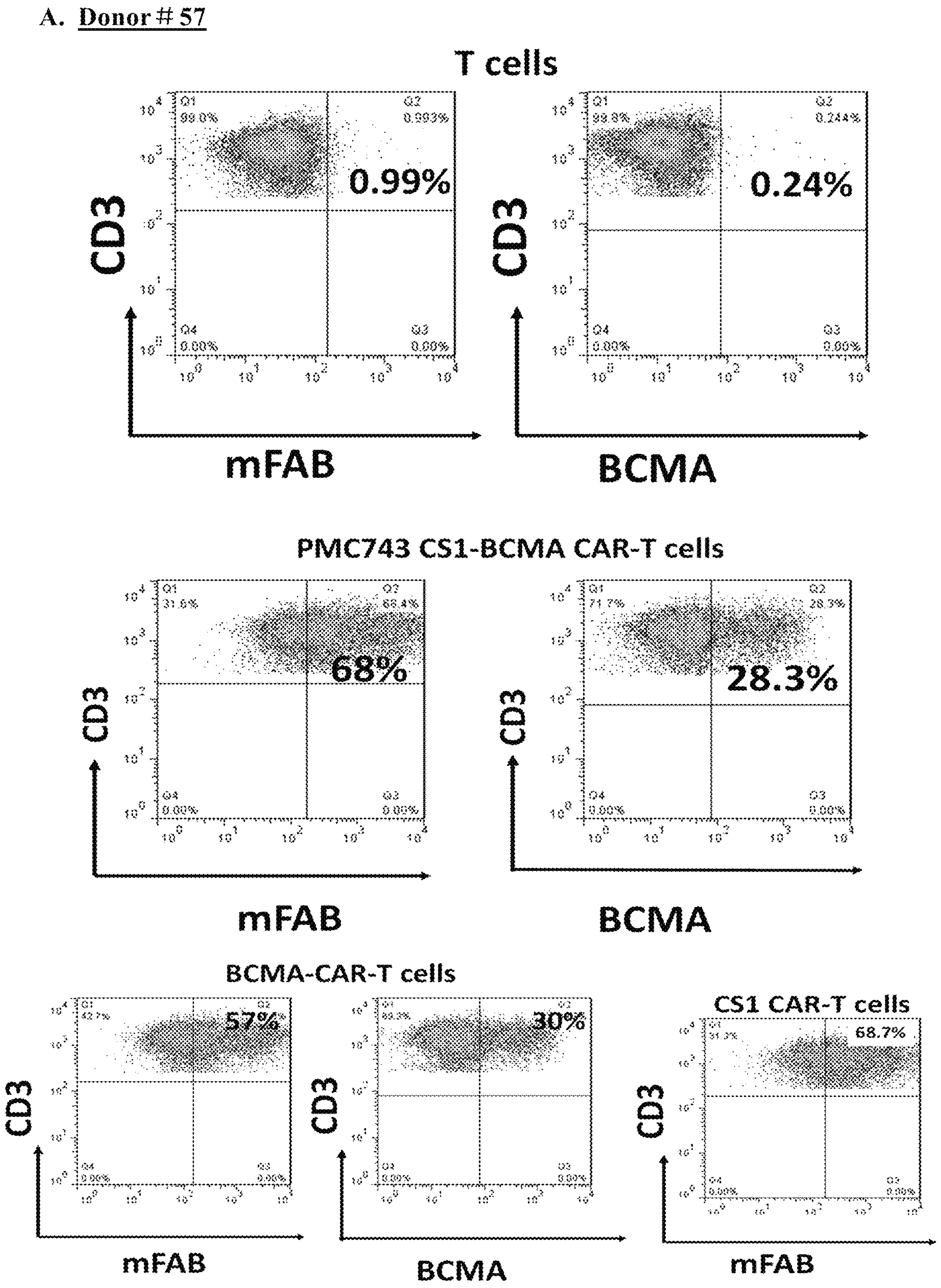
Figure 12:
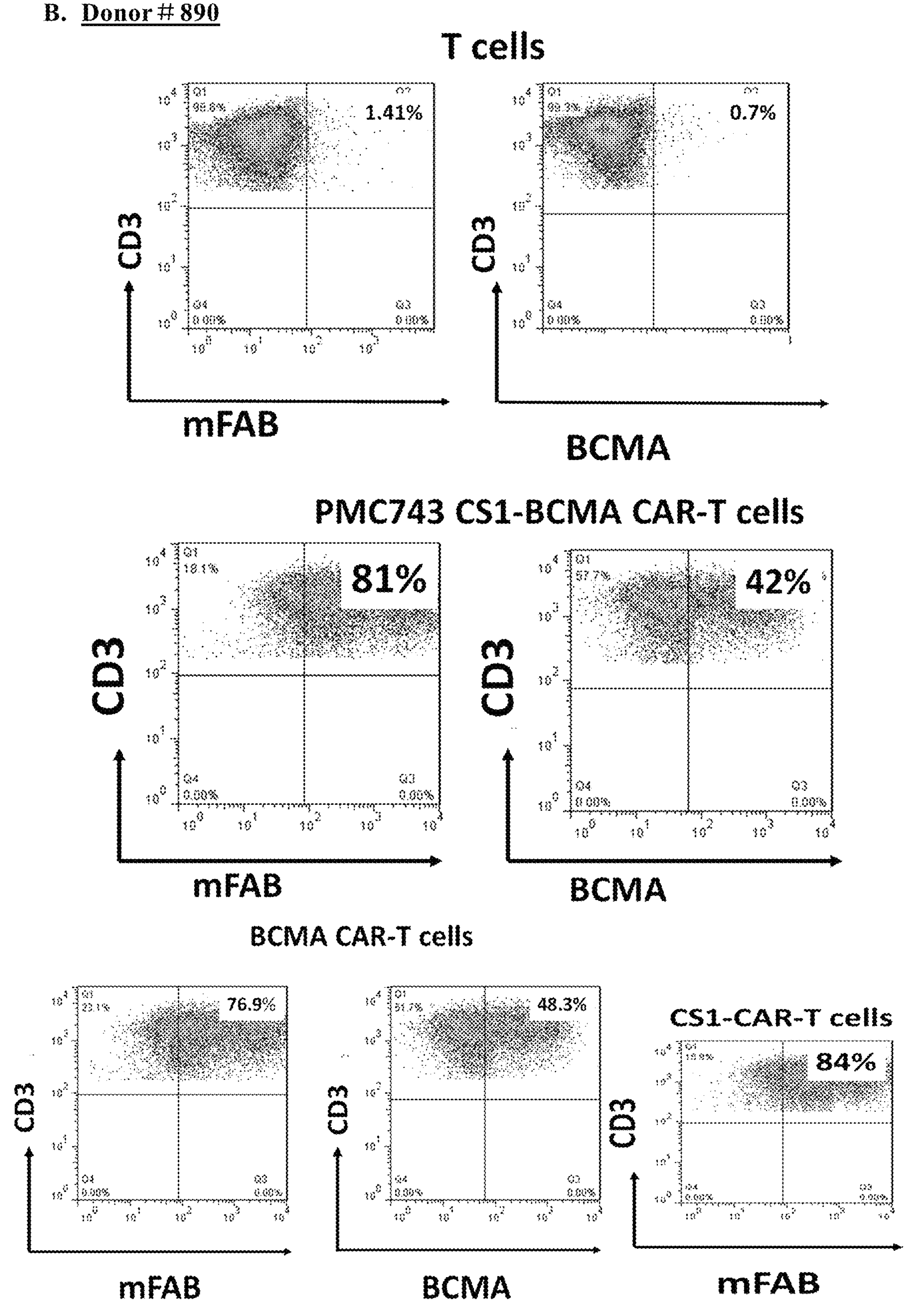
Figure 12:
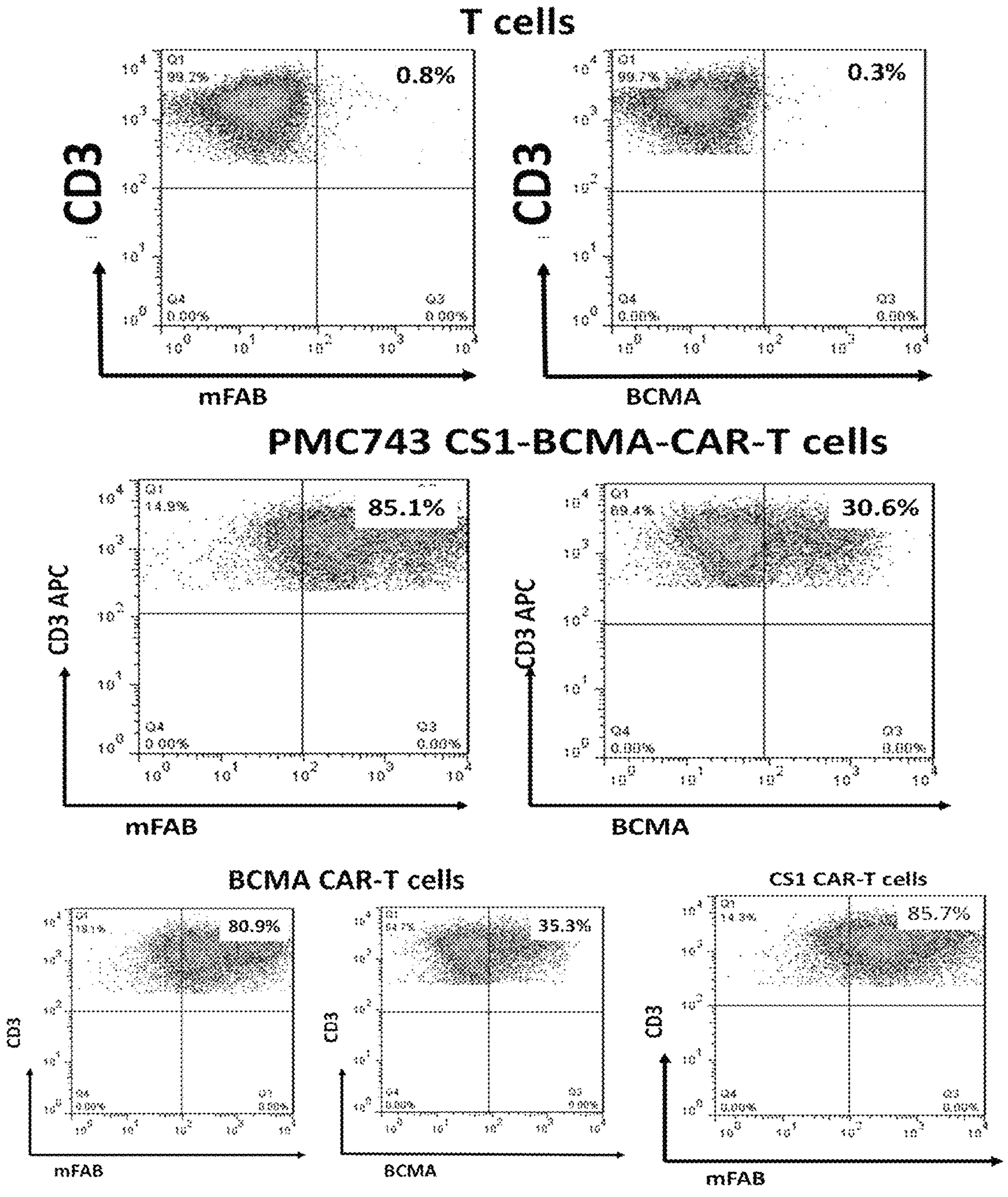

CAR-T cells from 3 donors were expanded to obtain CAR positive cells with high expression levels (FIG. 12).

Mouse F(ab)2 antibody was used for detection, and the proportion of PMC743 CAR cells of donor #57 was >70%. Biotinylated BCMA recombinant protein was used for detection, and the proportion was 28%. The results of single BCMA CAR-T cells were similar, in which the proportion of mFAB antibody detected was 57%, and the proportion of BCMA protein detected was 30%. There were 68% CAR+ cells in CS1 CAR-T cells, while control T cells were negative (FIG. 12A).

PMC743 CAR was transferred to donor #890. The results show that the proportion of CAR+ cells detected by mFAB was 81%, and the proportion detected by BCMA protein was 42% (FIG. 12B). Similar data were also obtained for the transduction of BCMA CAR and CS1 CAR based on donor #890, containing about 80% CAR+ cells.

A high percentage of CAR+ cells was also observed for PMC743 CAR transduction based on donor #999 (FIG. 12C).

The above results show that the PMC743 CAR of the present invention can be effectively transduced, so that CAR+ cells are expressed in a higher proportion.

Example 6 CS1-BCMA-CAR-T Cell Specifically Kill CS1 Positive Cells

The CS1-BCMA CAR-T cells of PBMC from 3 donors prepared in Example 5 were used for killing detection. Monospecific CS1-CAR-T cells and BCMA-CAR-T cells were prepared by a similar method and used as controls. Using CHO-BCMA and CHO-CS1 as target cells, the cytotoxicity assay was performed using a method similar to Example 2.

The results show that CS1-BCMA CAR-T cells can kill BCMA positive and CS1 positive cells at the same time (FIG. 13). The killing effect of CS1-BCMA cells is similar to that of BCMA-CAR-T cells on CHO-BCMA cells, and is similar or slightly lower than the killing effect of CS1-CAR-T cells from the same donor on CHO-CS1 cells. Since CS1-CAR-T cells do not kill CHO-BCMA cells and BCMA- CAR-T cells do not kill CHO-CS1 cells, the killing of each kind of CAR-T cells is specific.

The level of IFN-γ secretion was detected using a method similar to Example 4.

Figure 14:
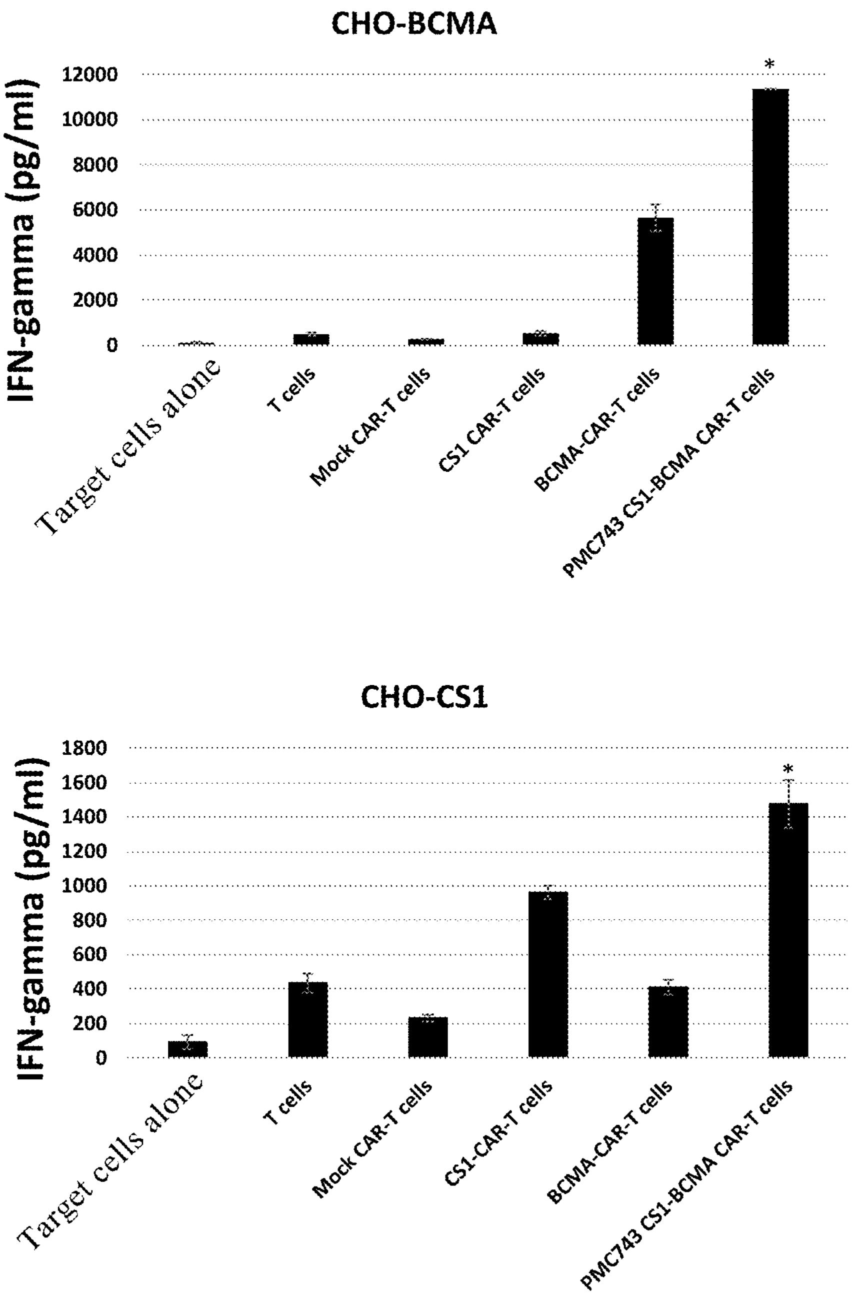
Figure 14:
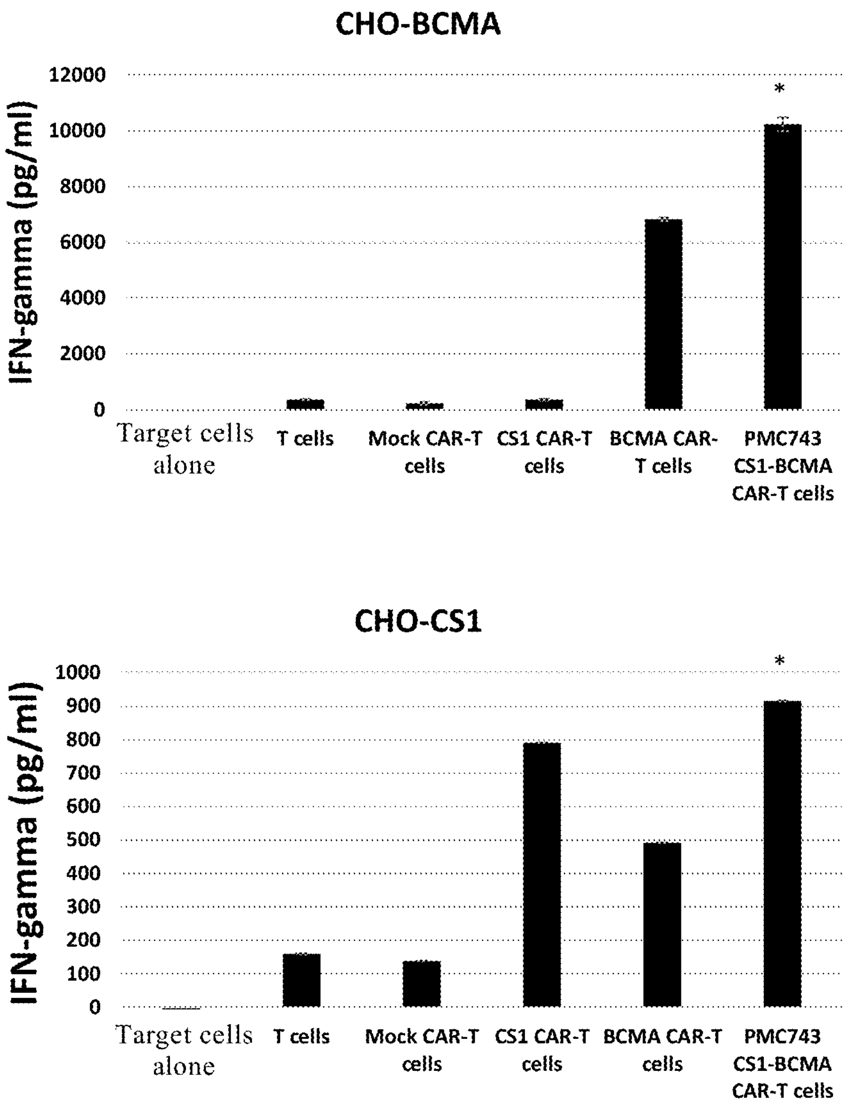

The results show that CS-1-BCMA-CAR-T cells secret high levels of IFN-γ against CS1-positive and BCMA-positive cells (FIG. 14). In CHO-BCMA cells, IFN-γ secretion of CS-1-BCMA-CAR-T cells is significantly higher than that of Mock CAR-T cells and higher than that of monospecific BCMA-CAR-T cells.

The IL-6 secretion was further analyzed. In terms of CRS safe CAR-T cells, all 3 donors had the lowest IL-6 level.

Example 7 In Vivo, CS1-BCMA-CAR-T Cells Significantly Block the Growth of RPMI8226 Xenograft Tumors Multiple myeloma RPMI8226 xenograft tumor model was used to analyze the in vivo killing of CS1-BCMA-CAR-T cells.

$2\times10^6$ RPMI8226-luciferase-positive cells (ATCC, CCL155™) were injected intravenously into NSG mice and $1\times10^7$ CS1-BCMA-CAR-T cells were injected intravenously the next day.

Figure 15:
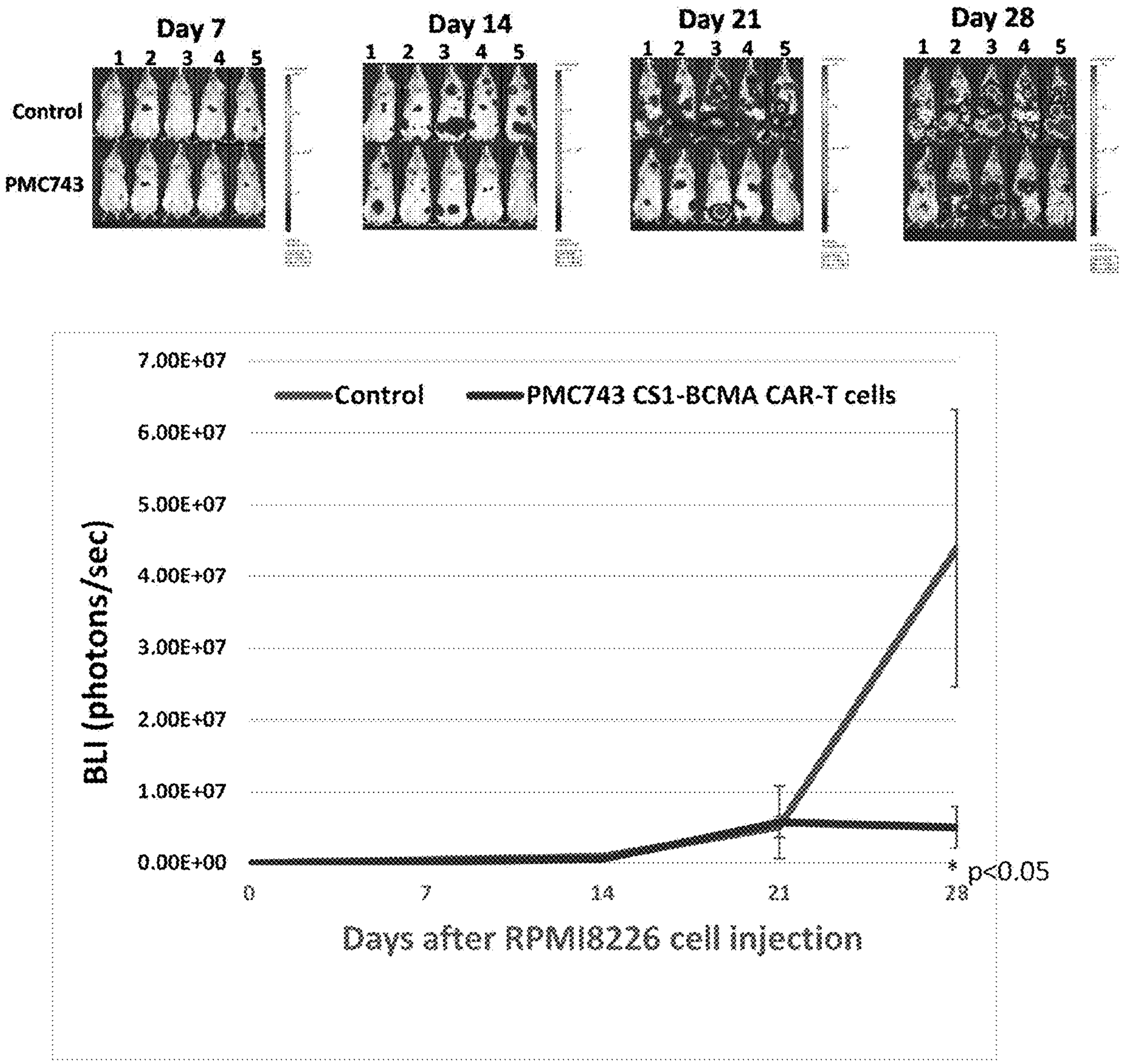
FIG. 15 shows that CS1-BCMA-CAR-T cells (PMC743) significantly inhibit the growth of RPMI8226 tumor cells. PMC743 treated mice were compared with control PBS treated mice, $p<0.05$.

The results show that CS1-BCMA-CAR-T cells significantly delayed tumor growth compared with the control group, $p<0.05$ (FIG. 15).

All references mentioned in the present application are incorporated by reference herein, as though individually incorporated by reference. In addition, it should be understood that after reading the above teaching content of the present invention, various changes or modifications may be made by those skilled in the art, and these equivalents also fall within the scope as defined by the appended claims of the present application.

The sequences and related informations involved in this application are as follows:

| SEQ ID NO. | Sequence name | Specific sequence |
|---|---|---|
| 1 | Anti-CS1 antibody heavy chain variable region | VQLQQSGPEVVRPGVSVKISCKGSGYTFTDYAIHW<br>VKQSHAKSLEWIGVINTYNGNTNYNQKFKGKATM<br>TVDKSSSTAYMELARLTSEDSAIYYCTRTGYYYGPS<br>HYFDYWGQGTTLTVSS |
| 2 | Anti-CS1 antibody light chain variable region | DIVLTQSPASLTVSLGQRATMSCRASKSVSTSGYSY<br>VHWYQQKPGQPPKLLIYLASNLESGVPARFSASGSG<br>TDFTLNIHPVEEEDAATYYCQHSRELPWTFGGGTKL<br>EIKR |
| 3 | Chimeric antigen receptor | VQLQQSGPEVVRPGVSVKISCKGSGYTFTDYAIHW<br>VKQSHAKSLEWIGVINTYNGNTNYNQKFKGKATM<br>TVDKSSSTAYMELARLTSEDSAIYYCTRTGYYYGPS<br>HYFDYWGQGTTLTVSSGGGGSGGGGSGGGGSDIVL<br>TQSPASLTVSLGQRATMSCRASKSVSTSGYSYVHW<br>YQQKPGQPPKLLIYLASNLESGVPARFSASGSGTDF<br>TLNIHPVEEEDAATYYCQHSRELPWTFGGGTKLEIK<br>RGGGGSGGGGSGGGGSDIVMTQSPATLSVTPGDRV<br>SLSCRASQSISDYLHWYQQKSHESPRLLIKYASQSIS<br>GIPSRFSGSGSGSDFTLSINSVEPEDVGVYYCQNGHS<br>FPPTFGGGTKLEIKGGGGGGGGSGGGGSQVQLQQ<br>SGPELVKPGASVKMSCKASGYTFTSYVMHWVKQK<br>PGQGLEWIGYIIPYNDATKYNEKFKGKATLTSDKSS<br>STAYMELSSLTSEDSAVYYCARYNYDGYFDVWGA<br>GTTVTVSSLEKTTTPAPRPPTPAPTIASQPLSLRPEAC<br>RPAAGGAVHTRGLDFASDKPFWVLVVVGGVLACY<br>SLLVTVAFIIFWVKRGRKKLLYIFKQPF**M**RPVQTTQ<br>EEDGCSCRFPEEEEGGCELRVKFSRSADAPAYKQGQ<br>NQLYNELNLGRREEYDVLDKRRGRDPE**M**GGKPRR<br>KNPQEGLYNELQKDK**M**AEAYSEIG**M**KGERRRGKG<br>HDGLYQGLSTATKDTYDALH**M**QALPPR |
| 4 | Anti-BCMA antibody heavy chain variable region | QVQLQQSGPELVKPGASVKMSCKASGYTFTSYVM<br>HWVKQKPGQGLEWIGYIIPYNDATKYNEKFKGKAT<br>LTSDKSSSTAYMELSSLTSEDSAVYYCARYNYDGY<br>FDVWGAGTTVTVSS |
| 5 | Anti-BCMA antibody light chain variable region | DIVMTQSPATLSVTPGDRVSLSCRASQSISDYLHWY<br>QQKSHESPRLLIKYASQSISGIPSRFSGSGSGSDFTLSI<br>NSVEPEDVGVYYCQNGHSFPPTFGGGTKLEIK |
| 6 | Linking peptide | GGGGS |
| 7 | Signal peptide | **M**ALPVTALLLPLALLLHAARP |

-continued

| SEQ ID NO. | Sequence name | Specific sequence |
|---|---|---|
| 8 | Hinge region | KTTTPAPRPPTPAPTIASQPLSLRPEACRPAAGGAVHTRGLDFASD |
| 9 | Transmembrane region | FWVLVVVGGVLACYSLLVTVAFIIFWV |
| 10 | Costimulatory signal molecule | KRGRKKLLYIFKQPFMRPVQTTQEEDGCSCRFPEEEEGGCEL |
| 11 | CD32ζ | RVKFSRSADAPAYKQGQNQLYNELNLGRREEYDVLDKRRGRDPE**M**GGKPRRKNPQEGLYNELQKDK**M**AEAYSEIG**M**KGERRRGKGHDGLYQGLSTATKDTYDALH**M**QALPPR |
| 12 | CS1 antigen | MAGSPTCLTLIYILWQLTGSAASGPVKELVGSVGGAVTFPLKSKVKQVDSIVWTFNTTPLVTIQPEGGTIIVTQNRNRERVDFPDGGYSLKLSKLKKNDSGIYYVGIYSSSLQQPSTQEYVLHVYEHLSKPKVTMGLQSNKNGTCVTNLTCCMEHGEEDVIYTWKALGQAANESHNGSILPISWRWGESDMTFICVARNPVSRNFSSPILARKLCEGAADDPDSSMVLLCLLLVPLLLSLFVLGLFLWFLKRERQEEYIEEKKRVDICRETPNICPHSGENTEYDTIPHTNRTILKEDPANTVYSTVEIPKKMENPHSLLTMPDTPRLFAYENVI |
| 13 | BCMA antigen | MLQMAGQCSQNEYFDSLLHACIPCQLRCSSNTPPLTCQRYCNASVTNSVKGTNAILWTCLGLSLIISLAVFVLMFLLRKINSEPLKDEFKNTGSGLLGMANIDLEKSRTGDEIILPRGLEYTVEECTCEDCIKSKPKVDSDHCFPLPAMEEGATILVTTKTNDYCKSLPAALSATEIEKSISAR |

The invention claimed is:

1. A bispecific chimeric antigen receptor (CAR), wherein the structure of the chimeric antigen receptor is shown in the following Formula I:

L-scFv1-I-scFv2-H-TM-C-CD3ζ (I)

wherein, each "-" is independently a linking peptide or a peptide bond;

L is an optional signal peptide sequence;

I is a flexible linker;

H is a hinge region;

TM is a transmembrane domain;

C is a costimulatory signal molecule;

CD3ζ is a cytoplasmic signaling sequence derived from CD3ζ;

scFv1 is an antigen binding domain targeting CS1, and scFv2 is an antigen binding domain targeting BCMA;

wherein the amino acid sequence of the heavy chain variable region of the antigen binding domain targeting CS1 is shown in SEQ ID NO: 1, and the amino acid sequence of the light chain variable region thereof is shown in SEQ ID NO: 2; and the amino acid sequence of the heavy chain variable region of the antigen binding domain targeting BCMA is shown in SEQ ID NO: 4, and the amino acid sequence of the light chain variable region thereof is shown in SEQ ID NO: 5.

2. The CAR of claim 1, wherein the structure of the antigen binding domain targeting CS1 is shown in the following Formula A:

$V_{H1}$-$V_{L1}$ (A);

wherein, $V_{H1}$ is an anti-CS1 antibody heavy chain variable region; $V_{L1}$ is an anti-CS1 antibody light chain variable region; and "-" is a linking peptide or a peptide bond.

3. The CAR of claim 1, wherein the structure of the antigen binding domain targeting BCMA is shown in the following Formula C:

$V_{L2}$-$V_{H2}$ (C);

wherein, $V_{L2}$ is an anti-BCMA antibody light chain variable region; $V_{H2}$ is an anti-BCMA antibody heavy chain variable region; and "-" is a linking peptide or a peptide bond.

4. The CAR of claim 1, wherein the amino acid sequence of the CAR is as shown in SEQ ID NO: 3.

5. A nucleic acid molecule encoding the CAR of claim 1.

6. A vector comprising the nucleic acid molecule of claim 5.

7. An engineered immune cell expressing the CAR of claim 1, wherein the engineered immune cell is a CAR-T cell or a CAR-NK cell.

8. A formulation comprising the CAR of claim 1, a nucleic acid molecule encoding the CAR, a vector comprising the nucleic acid molecule, or an immune cell expressing the CAR, and a pharmaceutically acceptable carrier, diluent or excipient.

9. A method for the preparation of an engineered immune cell expressing the CAR of claim 1, comprising:

(a) providing an immune cell to be modified, wherein the immune cell is a T cell or an NK cell; and (b) transferring a nucleic acid molecule encoding the CAR or a vector comprising the nucleic acid molecule into the immune cell to obtain the engineered immune cell.

10. A method of treating a disease, which comprises administering an appropriate amount of the engineered immune cell of claim 7 to a subject in need of treatment;

wherein the disease is at least one selected from the group consisting of a CSI positive tumor and a BCMA positive tumor.

11. The method of claim 10, wherein the disease is a hematological tumor.

12. The method of claim 11, wherein the disease is multiple myeloma (MM).

13. The CAR of claim 1, wherein the costimulatory signal molecule comprises a 4-1BB signaling domain.

14. The CAR of claim 13, wherein the cytoplasmic signaling sequence comprises a CD3ζ signaling sequence.

15. The CAR of claim 1, wherein the transmembrane domain is derived from CD28.

16. The CAR of claim 1, wherein the hinge region is derived from CD8.

17. The CAR of claim 1, wherein the signal peptide sequence is derived from CD8.

* * * * *

SEQUENCE LISTING

```
<160> NUMBER OF SEQ ID NOS: 13

<210> SEQ ID NO 1
<211> LENGTH: 121
<212> TYPE: PRT
<213> ORGANISM: Artificial Sequence
<220> FEATURE:
<223> OTHER INFORMATION: Anti-CS1 antibody heavy chain variable region

<400> SEQUENCE: 1

Val Gln Leu Gln Gln Ser Gly Pro Glu Val Val Arg Pro Gly Val Ser
1               5                   10                  15

Val Lys Ile Ser Cys Lys Gly Ser Gly Tyr Thr Phe Thr Asp Tyr Ala
            20                  25                  30

Ile His Trp Val Lys Gln Ser His Ala Lys Ser Leu Glu Trp Ile Gly
        35                  40                  45

Val Ile Asn Thr Tyr Asn Gly Asn Thr Asn Tyr Asn Gln Lys Phe Lys
    50                  55                  60

Gly Lys Ala Thr Met Thr Val Asp Lys Ser Ser Ser Thr Ala Tyr Met
65                  70                  75                  80

Glu Leu Ala Arg Leu Thr Ser Glu Asp Ser Ala Ile Tyr Tyr Cys Thr
                85                  90                  95

Arg Thr Gly Tyr Tyr Tyr Gly Pro Ser His Tyr Phe Asp Tyr Trp Gly
            100                 105                 110

Gln Gly Thr Thr Leu Thr Val Ser Ser
        115                 120
```

<210> SEQ ID NO 2
<211> LENGTH: 112
<212> TYPE: PRT
<213> ORGANISM: Artificial Sequence
<220> FEATURE:
<223> OTHER INFORMATION: Anti-CS1 antibody light chain variable region

<400> SEQUENCE: 2

```
Asp Ile Val Leu Thr Gln Ser Pro Ala Ser Leu Thr Val Ser Leu Gly
1               5                   10                  15

Gln Arg Ala Thr Met Ser Cys Arg Ala Ser Lys Ser Val Ser Thr Ser
            20                  25                  30

Gly Tyr Ser Tyr Val His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110
```

<210> SEQ ID NO 3
<211> LENGTH: 734
<212> TYPE: PRT
<213> ORGANISM: Artificial Sequence
<220> FEATURE:
<223> OTHER INFORMATION: CAR

<400> SEQUENCE: 3

```
Val Gln Leu Gln Gln Ser Gly Pro Glu Val Val Arg Pro Gly Val Ser
1               5                   10                  15

Val Lys Ile Ser Cys Lys Gly Ser Gly Tyr Thr Phe Thr Asp Tyr Ala
            20                  25                  30

Ile His Trp Val Lys Gln Ser His Ala Lys Ser Leu Glu Trp Ile Gly
        35                  40                  45

Val Ile Asn Thr Tyr Asn Gly Asn Thr Asn Tyr Asn Gln Lys Phe Lys
    50                  55                  60

Gly Lys Ala Thr Met Thr Val Asp Lys Ser Ser Ser Thr Ala Tyr Met
65                  70                  75                  80

Glu Leu Ala Arg Leu Thr Ser Glu Asp Ser Ala Ile Tyr Tyr Cys Thr
                85                  90                  95

Arg Thr Gly Tyr Tyr Tyr Gly Pro Ser His Tyr Phe Asp Tyr Trp Gly
            100                 105                 110

Gln Gly Thr Thr Leu Thr Val Ser Ser Gly Gly Gly Gly Ser Gly Gly
        115                 120                 125

Gly Gly Ser Gly Gly Gly Gly Ser Asp Ile Val Leu Thr Gln Ser Pro
    130                 135                 140

Ala Ser Leu Thr Val Ser Leu Gly Gln Arg Ala Thr Met Ser Cys Arg
145                 150                 155                 160

Ala Ser Lys Ser Val Ser Thr Ser Gly Tyr Ser Tyr Val His Trp Tyr
                165                 170                 175

Gln Gln Lys Pro Gly Gln Pro Pro Lys Leu Leu Ile Tyr Leu Ala Ser
            180                 185                 190

Asn Leu Glu Ser Gly Val Pro Ala Arg Phe Ser Ala Ser Gly Ser Gly
        195                 200                 205
```

-continued

```
Thr Asp Phe Thr Leu Asn Ile His Pro Val Glu Glu Glu Asp Ala Ala
    210                 215                 220

Thr Tyr Tyr Cys Gln His Ser Arg Glu Leu Pro Trp Thr Phe Gly Gly
225                 230                 235                 240

Gly Thr Lys Leu Glu Ile Lys Arg Gly Gly Gly Gly Ser Gly Gly Gly
                245                 250                 255

Gly Ser Gly Gly Gly Gly Ser Asp Ile Val Met Thr Gln Ser Pro Ala
            260                 265                 270

Thr Leu Ser Val Thr Pro Gly Asp Arg Val Ser Leu Ser Cys Arg Ala
        275                 280                 285

Ser Gln Ser Ile Ser Asp Tyr Leu His Trp Tyr Gln Gln Lys Ser His
    290                 295                 300

Glu Ser Pro Arg Leu Leu Ile Lys Tyr Ala Ser Gln Ser Ile Ser Gly
305                 310                 315                 320

Ile Pro Ser Arg Phe Ser Gly Ser Gly Ser Gly Ser Asp Phe Thr Leu
                325                 330                 335

Ser Ile Asn Ser Val Glu Pro Glu Asp Val Gly Val Tyr Tyr Cys Gln
            340                 345                 350

Asn Gly His Ser Phe Pro Pro Thr Phe Gly Gly Gly Thr Lys Leu Glu
        355                 360                 365

Ile Lys Gly Gly Gly Gly Ser Gly Gly Gly Gly Ser Gly Gly Gly Gly
    370                 375                 380

Ser Gln Val Gln Leu Gln Gln Ser Gly Pro Glu Leu Val Lys Pro Gly
385                 390                 395                 400

Ala Ser Val Lys Met Ser Cys Lys Ala Ser Gly Tyr Thr Phe Thr Ser
                405                 410                 415

Tyr Val Met His Trp Val Lys Gln Lys Pro Gly Gln Gly Leu Glu Trp
            420                 425                 430

Ile Gly Tyr Ile Ile Pro Tyr Asn Asp Ala Thr Lys Tyr Asn Glu Lys
        435                 440                 445

Phe Lys Gly Lys Ala Thr Leu Thr Ser Asp Lys Ser Ser Ser Thr Ala
    450                 455                 460

Tyr Met Glu Leu Ser Ser Leu Thr Ser Glu Asp Ser Ala Val Tyr Tyr
465                 470                 475                 480

Cys Ala Arg Tyr Asn Tyr Asp Gly Tyr Phe Asp Val Trp Gly Ala Gly
                485                 490                 495

Thr Thr Val Thr Val Ser Ser Leu Glu Lys Thr Thr Thr Pro Ala Pro
            500                 505                 510

Arg Pro Pro Thr Pro Ala Pro Thr Ile Ala Ser Gln Pro Leu Ser Leu
        515                 520                 525

Arg Pro Glu Ala Cys Arg Pro Ala Ala Gly Gly Ala Val His Thr Arg
    530                 535                 540

Gly Leu Asp Phe Ala Ser Asp Lys Pro Phe Trp Val Leu Val Val Val
545                 550                 555                 560

Gly Gly Val Leu Ala Cys Tyr Ser Leu Leu Val Thr Val Ala Phe Ile
                565                 570                 575

Ile Phe Trp Val Lys Arg Gly Arg Lys Lys Leu Leu Tyr Ile Phe Lys
            580                 585                 590

Gln Pro Phe Met Arg Pro Val Gln Thr Thr Gln Glu Glu Asp Gly Cys
        595                 600                 605

Ser Cys Arg Phe Pro Glu Glu Glu Glu Gly Gly Cys Glu Leu Arg Val
    610                 615                 620

Lys Phe Ser Arg Ser Ala Asp Ala Pro Ala Tyr Lys Gln Gly Gln Asn
```

```
625                 630                 635                 640

Gln Leu Tyr Asn Glu Leu Asn Leu Gly Arg Arg Glu Glu Tyr Asp Val
                645                 650                 655

Leu Asp Lys Arg Arg Gly Arg Asp Pro Glu Met Gly Gly Lys Pro Arg
            660                 665                 670

Arg Lys Asn Pro Gln Glu Gly Leu Tyr Asn Glu Leu Gln Lys Asp Lys
        675                 680                 685

Met Ala Glu Ala Tyr Ser Glu Ile Gly Met Lys Gly Glu Arg Arg Arg
    690                 695                 700

Gly Lys Gly His Asp Gly Leu Tyr Gln Gly Leu Ser Thr Ala Thr Lys
705                 710                 715                 720

Asp Thr Tyr Asp Ala Leu His Met Gln Ala Leu Pro Pro Arg
                725                 730


<210> SEQ ID NO 4
<211> LENGTH: 118
<212> TYPE: PRT
<213> ORGANISM: Artificial Sequence
<220> FEATURE:
<223> OTHER INFORMATION: Anti-BCMA antibody heavy chain variable region

<400> SEQUENCE: 4

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Ala Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Tyr Asn Tyr Asp Gly Tyr Phe Asp Val Trp Gly Ala Gly Thr
            100                 105                 110

Thr Val Thr Val Ser Ser
        115


<210> SEQ ID NO 5
<211> LENGTH: 107
<212> TYPE: PRT
<213> ORGANISM: Artificial Sequence
<220> FEATURE:
<223> OTHER INFORMATION: Anti-BCMA antibody light chain variable region

<400> SEQUENCE: 5

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80
```

```
Glu Asp Val Gly Val Tyr Tyr Cys Gln Asn Gly His Ser Phe Pro Pro
                85                  90                  95

Thr Phe Gly Gly Gly Thr Lys Leu Glu Ile Lys
            100                 105


<210> SEQ ID NO 6
<211> LENGTH: 5
<212> TYPE: PRT
<213> ORGANISM: Artificial Sequence
<220> FEATURE:
<223> OTHER INFORMATION: linking peptide

<400> SEQUENCE: 6

Gly Gly Gly Gly Ser
1               5


<210> SEQ ID NO 7
<211> LENGTH: 21
<212> TYPE: PRT
<213> ORGANISM: Artificial Sequence
<220> FEATURE:
<223> OTHER INFORMATION: Signal peptide

<400> SEQUENCE: 7

Met Ala Leu Pro Val Thr Ala Leu Leu Leu Pro Leu Ala Leu Leu Leu
1               5                   10                  15

His Ala Ala Arg Pro
            20


<210> SEQ ID NO 8
<211> LENGTH: 46
<212> TYPE: PRT
<213> ORGANISM: Artificial Sequence
<220> FEATURE:
<223> OTHER INFORMATION: Hinge region

<400> SEQUENCE: 8

Lys Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Ser Asp
        35                  40                  45


<210> SEQ ID NO 9
<211> LENGTH: 27
<212> TYPE: PRT
<213> ORGANISM: Artificial Sequence
<220> FEATURE:
<223> OTHER INFORMATION: Transmembrane region

<400> SEQUENCE: 9

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 10
<211> LENGTH: 42
<212> TYPE: PRT
<213> ORGANISM: Artificial Sequence
<220> FEATURE:
<223> OTHER INFORMATION: Costimulatory signal molecule

<400> SEQUENCE: 10
```

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 11
<211> LENGTH: 112
<212> TYPE: PRT
<213> ORGANISM: Artificial Sequence
<220> FEATURE:
<223> OTHER INFORMATION: CD3

<400> SEQUENCE: 11

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 12
<211> LENGTH: 335
<212> TYPE: PRT
<213> ORGANISM: Artificial Sequence
<220> FEATURE:
<223> OTHER INFORMATION: CS1 antigen

<400> SEQUENCE: 12

Met Ala Gly Ser Pro Thr Cys Leu Thr Leu Ile Tyr Ile Leu Trp Gln
1 5 10 15

Leu Thr Gly Ser Ala Ala Ser Gly Pro Val Lys Glu Leu Val Gly Ser
20 25 30

Val Gly Gly Ala Val Thr Phe Pro Leu Lys Ser Lys Val Lys Gln Val
35 40 45

Asp Ser Ile Val Trp Thr Phe Asn Thr Thr Pro Leu Val Thr Ile Gln
50 55 60

Pro Glu Gly Gly Thr Ile Ile Val Thr Gln Asn Arg Asn Arg Glu Arg
65 70 75 80

Val Asp Phe Pro Asp Gly Gly Tyr Ser Leu Lys Leu Ser Lys Leu Lys
85 90 95

Lys Asn Asp Ser Gly Ile Tyr Tyr Val Gly Ile Tyr Ser Ser Ser Leu
100 105 110

Gln Gln Pro Ser Thr Gln Glu Tyr Val Leu His Val Tyr Glu His Leu
115 120 125

Ser Lys Pro Lys Val Thr Met Gly Leu Gln Ser Asn Lys Asn Gly Thr
130 135 140

Cys Val Thr Asn Leu Thr Cys Cys Met Glu His Gly Glu Glu Asp Val

```
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335


<210> SEQ ID NO 13
<211> LENGTH: 184
<212> TYPE: PRT
<213> ORGANISM: Artificial Sequence
<220> FEATURE:
<223> OTHER INFORMATION: BCMA antigen

<400> SEQUENCE: 13

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140
```

-continued

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```